United States Patent
Auger et al.

(10) Patent No.: US 9,011,547 B2
(45) Date of Patent: Apr. 21, 2015

(54) KNEE PROSTHESIS SYSTEM

(75) Inventors: Daniel D. Auger, Fort Wayne, IN (US);
David P. Fitzpatrick, Dublin (IE);
Joseph G. Wyss, Fort Wayne, IN (US);
Abraham P. Wright, Winona Lake, IN (US); Christel M. Wagner, Plymouth, IN (US); Stephen A. Hazebrouck, Winona Lake, IN (US); Daren L. Deffenbaugh, Winona Lake, IN (US)

(73) Assignee: Depuy (Ireland), Cork (IE)

( * ) Notice: Subject to any disclaimer, the term of this patent is extended or adjusted under 35 U.S.C. 154(b) by 599 days.

(21) Appl. No.: 12/691,232

(22) Filed: Jan. 21, 2010

(65) Prior Publication Data
US 2011/0178605 A1 Jul. 21, 2011

(51) Int. Cl.
*A61F 2/38* (2006.01)
*A61F 2/30* (2006.01)

(52) U.S. Cl.
CPC .............. *A61F 2/389* (2013.01); *A61F 2/3868* (2013.01); *A61F 2/3877* (2013.01); *A61F 2/3886* (2013.01); *A61F 2002/30217* (2013.01); *A61F 2002/30604* (2013.01); *A61F 2002/30878* (2013.01); *A61F 2002/30884* (2013.01); *A61F 2230/0067* (2013.01)

(58) Field of Classification Search
CPC ....... A61F 2/38; A61F 2/3836; A61F 2/3845; A61F 2/385; A61F 2/3859; A61F 2/3868; A61F 2/3886; A61F 2/389
USPC .......... 623/20.15, 18.11, 20.14, 20.19, 20.21, 623/20.23, 20.24, 20.26–20.28, 20.31, 623/20.32, 20.35
See application file for complete search history.

(56) References Cited

U.S. PATENT DOCUMENTS

| 3,852,045 | A | 12/1974 | Wheeler |
| 3,855,638 | A | 12/1974 | Pilliar |
| 3,953,899 | A | 5/1976 | Charnley |
| 4,156,943 | A | 6/1979 | Collier |
| 4,206,516 | A | 6/1980 | Pilliar |
| 4,224,696 | A | 9/1980 | Murray |

(Continued)

FOREIGN PATENT DOCUMENTS

| DE | 4308563 A1 | 9/1994 |
| EP | 495340 A1 | 7/1992 |

(Continued)

OTHER PUBLICATIONS

Restoration® Modular Revision Hip System Surgical Protocol, Restoration® Modular Cone Body/Conical Distal Stem Femoral Components Using the Restoration® Modular Instrument System, brochure, (2005) Stryker, pp. 1-21.*

(Continued)

*Primary Examiner* — Christopher D Prone

(57) ABSTRACT

A knee prosthesis system for total knee replacement procedures includes a plurality of distinctly-sized femoral components, a plurality of distinctly-sized fixed tibial components, a plurality of distinctly-sized mobile tibial components, a plurality of fixed inserts, and a plurality of mobile inserts. Each of the mobile inserts is sized and shaped such that each may be optimally matched to one of the femoral components and may be used with any one of the mobile tibial components. Each of the fixed inserts is sized and shaped such that each may be optimally matched to one of the femoral components and may be used with any one of the fixed tibial components.

19 Claims, 12 Drawing Sheets

(56) References Cited

U.S. PATENT DOCUMENTS

| | | | |
|---|---|---|---|
| 4,224,697 | A | 9/1980 | Murray |
| 4,257,129 | A | 3/1981 | Volz |
| 4,612,160 | A | 9/1986 | Donlevy |
| 4,673,407 | A | 6/1987 | Martin |
| 4,714,474 | A | 12/1987 | Brooks, Jr. |
| 4,795,468 | A | 1/1989 | Hodorek |
| 4,808,185 | A | 2/1989 | Penenberg |
| 4,822,362 | A | 4/1989 | Walker |
| 4,838,891 | A | 6/1989 | Branemark |
| 4,938,769 | A | 7/1990 | Shaw |
| 4,944,757 | A | 7/1990 | Martinez |
| 4,944,760 | A | 7/1990 | Kenna |
| 4,950,298 | A | 8/1990 | Gustilo |
| 4,963,152 | A | 10/1990 | Hofmann |
| 4,990,163 | A | 2/1991 | Ducheyne |
| 5,019,103 | A | 5/1991 | Van Zile |
| 5,037,423 | A | 8/1991 | Kenna |
| 5,080,675 | A | 1/1992 | Lawes |
| 5,104,410 | A | 4/1992 | Chowdhary |
| 5,108,442 | A | 4/1992 | Smith |
| 5,171,283 | A | 12/1992 | Pappas |
| 5,194,066 | A | 3/1993 | Van Zile |
| 5,198,308 | A | 3/1993 | Shetty |
| 5,201,766 | A | 4/1993 | Georgette |
| 5,251,468 | A | 10/1993 | Lin |
| 5,258,044 | A | 11/1993 | Lee |
| 5,263,987 | A | 11/1993 | Shah |
| 5,271,737 | A | 12/1993 | Baldwin |
| 5,282,861 | A | 2/1994 | Kaplan |
| 5,308,556 | A | 5/1994 | Bagley |
| 5,309,639 | A | 5/1994 | Lee |
| 5,326,361 | A | 7/1994 | Hollister |
| 5,326,365 | A | 7/1994 | Alvine |
| 5,330,534 | A | 7/1994 | Herrington |
| 5,344,460 | A | 9/1994 | Turanyi |
| 5,344,461 | A | 9/1994 | Phlipot |
| 5,344,494 | A | 9/1994 | Davidson |
| 5,358,531 | A | 10/1994 | Goodfellow et al. |
| 5,368,881 | A | 11/1994 | Kelman |
| 5,370,699 | A | 12/1994 | Hood |
| 5,387,240 | A | 2/1995 | Pottenger |
| 5,405,396 | A | 4/1995 | Heldreth |
| 5,413,604 | A | 5/1995 | Hodge |
| 5,414,049 | A | 5/1995 | Sun |
| 5,443,510 | A | 8/1995 | Shetty et al. |
| 5,449,745 | A | 9/1995 | Sun |
| 5,458,637 | A | 10/1995 | Hayes |
| 5,480,446 | A | 1/1996 | Goodfellow |
| 5,543,471 | A | 8/1996 | Sun |
| 5,571,187 | A | 11/1996 | Devanathan |
| 5,609,639 | A | 3/1997 | Walker |
| 5,609,641 | A | 3/1997 | Johnson et al. |
| 5,632,745 | A | 5/1997 | Schwartz |
| 5,650,485 | A | 7/1997 | Sun |
| 5,658,333 | A | 8/1997 | Kelman |
| 5,658,342 | A | 8/1997 | Draganich |
| 5,658,344 | A | 8/1997 | Hurlburt |
| 5,683,472 | A | 11/1997 | O'Neil |
| 5,690,636 | A | 11/1997 | Wildgoose |
| 5,702,447 | A | 12/1997 | Walch |
| 5,702,458 | A | 12/1997 | Burstein |
| 5,702,463 | A | 12/1997 | Pothier |
| 5,702,464 | A | 12/1997 | Lackey |
| 5,728,748 | A | 3/1998 | Sun |
| 5,732,469 | A | 3/1998 | Hamamoto |
| 5,749,874 | A | 5/1998 | Schwartz |
| 5,755,800 | A | 5/1998 | O'Neil |
| 5,755,801 | A | 5/1998 | Walker |
| 5,755,803 | A | 5/1998 | Haines |
| 5,755,808 | A | 5/1998 | DeCarlo |
| 5,759,190 | A | 6/1998 | Vibe Hansen |
| 5,765,095 | A | 6/1998 | Flak |
| 5,766,257 | A | 6/1998 | Goodman |
| 5,769,899 | A | 6/1998 | Schwartz |
| 5,800,546 | A | 9/1998 | Marik |
| 5,824,100 | A | 10/1998 | Kester |
| 5,824,103 | A | 10/1998 | Williams |
| 5,871,545 | A | 2/1999 | Goodfellow |
| 5,871,546 | A | 2/1999 | Colleran |
| 5,879,387 | A | 3/1999 | Jones |
| 5,879,394 | A | 3/1999 | Ashby |
| 5,879,400 | A | 3/1999 | Merrill |
| 5,906,577 | A | 5/1999 | Beane |
| 5,906,596 | A | 5/1999 | Tallarida |
| 5,906,644 | A | 5/1999 | Powell |
| 5,951,603 | A | 9/1999 | O'Neil |
| 5,954,564 | A | 9/1999 | Ganz |
| 5,957,979 | A | 9/1999 | Beckman |
| 5,964,808 | A | 10/1999 | Blaha |
| 5,976,147 | A | 11/1999 | LaSalle |
| 5,984,969 | A | 11/1999 | Matthews |
| 5,989,027 | A | 11/1999 | Wagner |
| 5,997,577 | A | 12/1999 | Herrington |
| 6,004,351 | A | 12/1999 | Tomita |
| 6,005,018 | A | 12/1999 | Cicierega |
| 6,010,534 | A | 1/2000 | O'Neil |
| 6,017,975 | A | 1/2000 | Saum |
| 6,039,764 | A | 3/2000 | Pottenger |
| 6,042,780 | A | 3/2000 | Huang |
| 6,053,945 | A | 4/2000 | O'Neil |
| 6,059,949 | A | 5/2000 | Gal Or |
| 6,068,658 | A | 5/2000 | Insall |
| 6,090,144 | A | 7/2000 | Letot |
| 6,123,728 | A | 9/2000 | Brosnahan |
| 6,123,896 | A | 9/2000 | Meeks, III |
| 6,126,692 | A | 10/2000 | Robie |
| 6,132,468 | A | 10/2000 | Mansmann |
| 6,135,857 | A | 10/2000 | Shaw |
| 6,139,581 | A | 10/2000 | Engh |
| 6,142,936 | A | 11/2000 | Beane |
| 6,162,254 | A | 12/2000 | Timoteo |
| 6,171,340 | B1 | 1/2001 | McDowell |
| 6,174,934 | B1 | 1/2001 | Sun |
| 6,179,876 | B1 | 1/2001 | Stamper |
| 6,210,444 | B1 | 4/2001 | Webster |
| 6,210,445 | B1 | 4/2001 | Zawadzki |
| 6,217,618 | B1 | 4/2001 | Hileman |
| 6,228,900 | B1 | 5/2001 | Shen |
| 6,238,434 | B1 | 5/2001 | Pappas |
| 6,242,507 | B1 | 6/2001 | Saum |
| 6,245,276 | B1 | 6/2001 | McNulty |
| 6,251,143 | B1 | 6/2001 | Schwartz |
| 6,258,127 | B1 | 7/2001 | Schmotzer |
| 6,280,476 | B1 | 8/2001 | Metzger |
| 6,281,264 | B1 | 8/2001 | Salovey |
| 6,299,646 | B1 | 10/2001 | Chambat |
| 6,316,158 | B1 | 11/2001 | Saum |
| 6,319,283 | B1 | 11/2001 | Insall |
| 6,344,059 | B1 | 2/2002 | Krakovits |
| 6,352,558 | B1 | 3/2002 | Spector |
| 6,361,564 | B1 | 3/2002 | Marceaux |
| 6,372,814 | B1 | 4/2002 | Sun |
| 6,379,388 | B1 | 4/2002 | Ensign |
| 6,428,577 | B1 | 8/2002 | Evans |
| 6,440,063 | B1 | 8/2002 | Beane |
| 6,443,991 | B1 | 9/2002 | Running |
| 6,468,314 | B2 | 10/2002 | Schwartz |
| 6,485,519 | B2 | 11/2002 | Meyers |
| 6,494,914 | B2 | 12/2002 | Brown |
| 6,503,280 | B2 | 1/2003 | Repicci |
| 6,506,215 | B1 | 1/2003 | Letot |
| 6,506,216 | B1 | 1/2003 | McCue |
| 6,520,964 | B2 | 2/2003 | Tallarida |
| 6,524,522 | B2 | 2/2003 | Vaidyanathan |
| 6,527,754 | B1 | 3/2003 | Tallarida |
| 6,569,202 | B2 | 5/2003 | Whiteside |
| 6,582,470 | B1 | 6/2003 | Lee |
| 6,589,283 | B1 * | 7/2003 | Metzger et al. ............ 623/20.35 |
| 6,592,787 | B2 | 7/2003 | Pickrell |
| 6,620,198 | B2 | 9/2003 | Burstein |
| 6,623,526 | B1 | 9/2003 | Lloyd |
| 6,626,950 | B2 | 9/2003 | Brown |
| 6,645,251 | B2 | 11/2003 | Salehi |
| 6,652,592 | B1 | 11/2003 | Grooms |

(56) References Cited

U.S. PATENT DOCUMENTS

| | | |
|---|---|---|
| 6,660,039 B1 | 12/2003 | Evans et al. |
| 6,660,224 B2 | 12/2003 | Lefebvre |
| 6,664,308 B2 | 12/2003 | Sun |
| 6,679,917 B2 | 1/2004 | Ek |
| 6,699,291 B1 | 3/2004 | Augoyard et al. |
| 6,702,821 B2 | 3/2004 | Bonutti |
| 6,716,249 B2 | 4/2004 | Hyde |
| 6,719,800 B2 | 4/2004 | Meyers |
| 6,726,724 B2 | 4/2004 | Repicci |
| 6,755,864 B1 | 6/2004 | Brack et al. |
| 6,773,461 B2 | 8/2004 | Meyers |
| 6,783,548 B2 | 8/2004 | Hyde, Jr. |
| 6,818,020 B2 | 11/2004 | Sun |
| 6,846,327 B2 | 1/2005 | Khandkar |
| 6,849,230 B1 | 2/2005 | Feichtinger |
| 6,852,272 B2 | 2/2005 | Artz |
| 6,869,448 B2 | 3/2005 | Tuke |
| 6,875,235 B2 | 4/2005 | Ferree |
| 6,923,832 B1 | 8/2005 | Sharkey |
| 6,942,670 B2 | 9/2005 | Heldreth |
| 6,945,448 B2 | 9/2005 | Medlin |
| 6,953,479 B2 | 10/2005 | Carson |
| 6,972,039 B2 | 12/2005 | Metzger |
| 6,984,248 B2 | 1/2006 | Hyde, Jr. |
| 6,986,791 B1 | 1/2006 | Metzger |
| 6,994,730 B2 | 2/2006 | Posner |
| 7,025,788 B2 | 4/2006 | Metzger |
| 7,048,741 B2 | 5/2006 | Swanson |
| 7,070,622 B1 | 7/2006 | Brown |
| 7,077,867 B1 | 7/2006 | Pope |
| 7,087,082 B2 | 8/2006 | Paul |
| 7,094,259 B2 | 8/2006 | Tarabichi |
| 7,101,401 B2 | 9/2006 | Brack |
| 7,108,720 B2 | 9/2006 | Hanes |
| 7,147,819 B2 | 12/2006 | Bram |
| 7,175,665 B2 | 2/2007 | German |
| 7,208,013 B1 | 4/2007 | Bonutti |
| 7,255,715 B2 | 8/2007 | Metzger |
| 7,278,997 B1 | 10/2007 | Mueller |
| 7,294,149 B2 | 11/2007 | Hozack |
| 7,297,164 B2 | 11/2007 | Johnson |
| 7,338,529 B1 | 3/2008 | Higgins |
| 7,341,602 B2 | 3/2008 | Fell et al. |
| 7,344,460 B2 | 3/2008 | Gait |
| 7,357,817 B2 | 4/2008 | D'Alessio, II |
| 7,445,639 B2 | 11/2008 | Metzger |
| 7,494,507 B2 | 2/2009 | Dixon |
| 7,497,874 B1 | 3/2009 | Metzger |
| 7,527,631 B2 | 5/2009 | Maroney et al. |
| 7,527,650 B2 | 5/2009 | Johnson |
| 7,563,286 B2 | 7/2009 | Gerber |
| 7,572,295 B2 | 8/2009 | Steinberg |
| 7,578,850 B2 | 8/2009 | Kuczynski |
| 7,608,079 B1 | 10/2009 | Blackwell |
| 7,611,519 B2 | 11/2009 | Lefevre |
| 7,618,462 B2 | 11/2009 | Ek |
| 7,628,817 B1 | 12/2009 | Axelson, Jr. |
| 7,628,818 B2 | 12/2009 | Hazebrouck |
| 7,635,390 B1 | 12/2009 | Bonutti |
| 7,695,519 B2 | 4/2010 | Collazo |
| 7,740,662 B2 | 6/2010 | Barnett |
| 7,748,984 B2 | 7/2010 | McAllister |
| 7,749,229 B1 | 7/2010 | Bonutti |
| 7,753,960 B2 | 7/2010 | Cipolletti |
| 7,758,653 B2 | 7/2010 | Steinberg |
| 7,766,911 B1 | 8/2010 | Navarro |
| 7,771,484 B2 | 8/2010 | Campbell |
| 7,776,044 B2 | 8/2010 | Pendleton |
| 7,780,666 B1 | 8/2010 | Navarro |
| 7,780,674 B2 | 8/2010 | Medley et al. |
| 7,785,327 B1 | 8/2010 | Navarro |
| 7,790,779 B2 | 9/2010 | Muratoglu |
| 7,803,193 B2 | 9/2010 | Steinberg |
| 7,833,245 B2 | 11/2010 | Kaes |
| 7,951,204 B2 | 5/2011 | Chambat et al. |
| 7,978,151 B2 | 7/2011 | Taira |
| 7,978,152 B2 | 7/2011 | Huang |
| 7,981,159 B2 | 7/2011 | Williams et al. |
| 8,066,770 B2 | 11/2011 | Rivard |
| 8,128,703 B2 | 3/2012 | Hazebrouck et al. |
| 8,187,335 B2 | 5/2012 | Wyss |
| 8,192,498 B2 | 6/2012 | Wagner |
| 8,206,451 B2 | 6/2012 | Wyss |
| 8,236,061 B2 | 8/2012 | Heldreth |
| 8,366,782 B2 | 2/2013 | Wright |
| 8,470,047 B2 | 6/2013 | Hazebrouck |
| 8,545,570 B2 | 10/2013 | Crabtree et al. |
| 8,591,594 B2 | 11/2013 | Parisi et al. |
| 8,603,101 B2 | 12/2013 | Claypool et al. |
| 8,617,250 B2 | 12/2013 | Metzger |
| 8,632,600 B2 | 1/2014 | Zannis |
| 8,658,710 B2 | 2/2014 | McKellop |
| 8,715,359 B2 | 5/2014 | Deffenbaugh |
| 8,715,362 B2 | 5/2014 | Reiley |
| 8,727,203 B2 | 5/2014 | Wang |
| 2001/0010023 A1 | 7/2001 | Schwartz |
| 2002/0120274 A1 | 8/2002 | Overaker |
| 2002/0173855 A1 | 11/2002 | Mansmann |
| 2003/0004578 A1 | 1/2003 | Brown |
| 2003/0014122 A1 | 1/2003 | Whiteside |
| 2003/0035747 A1 | 2/2003 | Anderson |
| 2003/0036801 A1 | 2/2003 | Schwartz |
| 2003/0044301 A1 | 3/2003 | Lefebvre |
| 2003/0075013 A1 | 4/2003 | Grohowski |
| 2003/0139817 A1 | 7/2003 | Tuke |
| 2003/0153981 A1 | 8/2003 | Wang |
| 2003/0171820 A1 | 9/2003 | Wilshaw |
| 2003/0212161 A1 | 11/2003 | McKellop |
| 2003/0220700 A1 | 11/2003 | Hammer |
| 2003/0225456 A1 | 12/2003 | Ek |
| 2004/0015770 A1 | 1/2004 | Kimoto |
| 2004/0019384 A1 | 1/2004 | Kirking |
| 2004/0039450 A1 | 2/2004 | Griner |
| 2004/0167633 A1 | 8/2004 | Wen |
| 2004/0186583 A1 | 9/2004 | Keller |
| 2004/0215345 A1 | 10/2004 | Perrone |
| 2005/0015153 A1 | 1/2005 | Goble |
| 2005/0021147 A1 | 1/2005 | Tarabichi |
| 2005/0055102 A1 | 3/2005 | Tornier |
| 2005/0059750 A1 | 3/2005 | Sun |
| 2005/0064042 A1 | 3/2005 | Vunjak Novakovic |
| 2005/0069629 A1 | 3/2005 | Becker |
| 2005/0100578 A1 | 5/2005 | Schmid |
| 2005/0123672 A1 | 6/2005 | Justin |
| 2005/0125068 A1 | 6/2005 | Hozack |
| 2005/0192672 A1 | 9/2005 | Wyss et al. |
| 2005/0203631 A1 | 9/2005 | Daniels |
| 2005/0209702 A1 | 9/2005 | Todd |
| 2005/0249625 A1 | 11/2005 | Bram |
| 2006/0002810 A1 | 1/2006 | Grohowski |
| 2006/0015185 A1 | 1/2006 | Chambat et al. |
| 2006/0030945 A1 | 2/2006 | Wright |
| 2006/0036329 A1 | 2/2006 | Webster |
| 2006/0047283 A1 | 3/2006 | Evans |
| 2006/0052875 A1 | 3/2006 | Bernero |
| 2006/0100714 A1 | 5/2006 | Ensign |
| 2006/0111790 A1 | 5/2006 | Dietz |
| 2006/0195195 A1 | 8/2006 | Burstein |
| 2006/0228247 A1 | 10/2006 | Grohowski |
| 2006/0231402 A1 | 10/2006 | Clasen |
| 2006/0241781 A1 | 10/2006 | Brown |
| 2006/0257358 A1 | 11/2006 | Wen |
| 2006/0271191 A1 | 11/2006 | Hermansson |
| 2006/0289388 A1 | 12/2006 | Yang |
| 2007/0061014 A1 | 3/2007 | Naegerl |
| 2007/0073409 A1 | 3/2007 | Cooney |
| 2007/0078521 A1 | 4/2007 | Overholser |
| 2007/0100463 A1 | 5/2007 | Aram |
| 2007/0129809 A1 | 6/2007 | Meridew |
| 2007/0162143 A1 | 7/2007 | Wasielewski |
| 2007/0162144 A1 | 7/2007 | Wasielewski |
| 2007/0173948 A1 | 7/2007 | Meridew |
| 2007/0196230 A1 | 8/2007 | Hamman |
| 2007/0203582 A1 | 8/2007 | Campbell |

(56) References Cited

U.S. PATENT DOCUMENTS

| | | |
|---|---|---|
| 2007/0219639 A1 | 9/2007 | Otto |
| 2007/0293647 A1 | 12/2007 | McKellop |
| 2008/0004708 A1 | 1/2008 | Wyss |
| 2008/0021567 A1 | 1/2008 | Meulink |
| 2008/0051908 A1 | 2/2008 | Angibaud et al. |
| 2008/0058945 A1 | 3/2008 | Hajaj et al. |
| 2008/0091272 A1 | 4/2008 | Aram |
| 2008/0097616 A1 | 4/2008 | Meyers |
| 2008/0114462 A1 | 5/2008 | Guidera |
| 2008/0114464 A1 | 5/2008 | Barnett |
| 2008/0119940 A1 | 5/2008 | Otto |
| 2008/0133019 A1 | 6/2008 | Andrysek |
| 2008/0161927 A1 | 7/2008 | Savage |
| 2008/0195108 A1 | 8/2008 | Bhatnagar |
| 2008/0199720 A1 | 8/2008 | Liu |
| 2008/0206297 A1 | 8/2008 | Roeder |
| 2009/0048680 A1 | 2/2009 | Naegerl |
| 2009/0082873 A1 | 3/2009 | Hazebrouck |
| 2009/0084491 A1 | 4/2009 | Uthgenannt |
| 2009/0088859 A1 | 4/2009 | Hazebrouck |
| 2009/0125114 A1 | 5/2009 | May |
| 2009/0125115 A1 | 5/2009 | Popoola |
| 2009/0149964 A1 | 6/2009 | May |
| 2009/0182433 A1 | 7/2009 | Reiley et al. |
| 2009/0192610 A1 | 7/2009 | Case |
| 2009/0264894 A1 | 10/2009 | Wasielewski |
| 2009/0265012 A1 | 10/2009 | Engh |
| 2009/0265013 A1 | 10/2009 | Mandell |
| 2009/0292365 A1 | 11/2009 | Smith |
| 2009/0295035 A1 | 12/2009 | Evans |
| 2009/0326663 A1 | 12/2009 | Dun |
| 2009/0326664 A1 | 12/2009 | Wagner |
| 2009/0326665 A1 | 12/2009 | Wyss |
| 2009/0326666 A1 | 12/2009 | Wyss |
| 2009/0326667 A1 | 12/2009 | Williams |
| 2009/0326674 A1 | 12/2009 | Liu |
| 2010/0016979 A1 | 1/2010 | Wyss |
| 2010/0036499 A1 | 2/2010 | Pinskerova |
| 2010/0036500 A1 | 2/2010 | Heldreth |
| 2010/0042224 A1 | 2/2010 | Otto |
| 2010/0042225 A1 | 2/2010 | Shur |
| 2010/0063594 A1 | 3/2010 | Hazebrouck |
| 2010/0070045 A1 | 3/2010 | Ek |
| 2010/0076563 A1 | 3/2010 | Otto |
| 2010/0076564 A1 | 3/2010 | Schilling |
| 2010/0076569 A1 | 3/2010 | Langhorn |
| 2010/0094429 A1 | 4/2010 | Otto |
| 2010/0098574 A1 | 4/2010 | Liu |
| 2010/0100189 A1 | 4/2010 | Metzger |
| 2010/0100190 A1 | 4/2010 | May |
| 2010/0100191 A1 | 4/2010 | May |
| 2010/0114322 A1 | 5/2010 | Clifford |
| 2010/0125337 A1 | 5/2010 | Grecco |
| 2010/0161067 A1 | 6/2010 | Saleh |
| 2010/0191341 A1 | 7/2010 | Byrd |
| 2010/0222890 A1 | 9/2010 | Barnett |
| 2010/0262144 A1 | 10/2010 | Kelman |
| 2010/0262253 A1 | 10/2010 | Cipolletti et al. |
| 2010/0286788 A1 | 11/2010 | Komistek |
| 2010/0292804 A1 | 11/2010 | Samuelson |
| 2010/0305710 A1 | 12/2010 | Metzger |
| 2010/0312350 A1 | 12/2010 | Bonutti |
| 2011/0029090 A1 | 2/2011 | Zannis |
| 2011/0029092 A1 | 2/2011 | Deruntz |
| 2011/0035017 A1 | 2/2011 | Deffenbaugh |
| 2011/0035018 A1 | 2/2011 | Deffenbaugh |
| 2011/0046735 A1 | 2/2011 | Metzger et al. |
| 2011/0106268 A1 | 5/2011 | Deffenbaugh |
| 2011/0178606 A1 | 7/2011 | Deffenbaugh et al. |
| 2011/0190897 A1 | 8/2011 | Guidera et al. |
| 2012/0067853 A1 | 3/2012 | Wang et al. |
| 2012/0296438 A1 | 11/2012 | Metzger et al. |
| 2012/0323333 A1 | 12/2012 | Metzger |
| 2013/0079885 A1 | 3/2013 | Meier et al. |
| 2013/0173009 A1 | 7/2013 | Hershberger |
| 2013/0184829 A1 | 7/2013 | Wyss et al. |
| 2013/0184830 A1 | 7/2013 | Hazebrouck et al. |

FOREIGN PATENT DOCUMENTS

| | | |
|---|---|---|
| EP | 634156 A2 | 1/1995 |
| EP | 636352 A2 | 2/1995 |
| EP | 634156 A3 | 4/1995 |
| EP | 732092 A2 | 9/1996 |
| EP | 732092 A3 | 1/1997 |
| EP | 765645 A2 | 4/1997 |
| EP | 765645 A3 | 11/1997 |
| EP | 634156 B1 | 5/1999 |
| EP | 636352 B1 | 1/2002 |
| EP | 732092 B1 | 2/2002 |
| EP | 1186277 A2 | 3/2002 |
| EP | 1226799 A1 | 7/2002 |
| EP | 765645 B1 | 8/2003 |
| EP | 1186277 A3 | 10/2003 |
| EP | 1421918 A1 | 5/2004 |
| EP | 1226799 B1 | 5/2005 |
| EP | 1186277 B1 | 10/2005 |
| EP | 1779812 A1 | 5/2007 |
| EP | 1923079 A1 | 5/2008 |
| FR | 2653992 A1 | 5/1991 |
| FR | 2780636 A1 | 1/2000 |
| FR | 2837093 A1 | 9/2003 |
| GB | 1065354 A | 4/1967 |
| GB | 2293109 A | 3/1996 |
| JP | 62205201 A | 9/1987 |
| JP | 10137271 A | 5/1998 |
| JP | 02272756 A | 9/2002 |
| JP | 02315757 A | 10/2002 |
| WO | WO 9014806 A1 | 12/1990 |
| WO | WO 9524874 A1 | 9/1995 |
| WO | WO 9530388 A1 | 11/1995 |
| WO | WO 9624302 A1 | 8/1996 |
| WO | WO 9624304 A1 | 8/1996 |
| WO | WO 9725742 A1 | 7/1997 |
| WO | WO 9966864 A1 | 12/1999 |
| WO | WO 03039609 A1 | 5/2003 |
| WO | WO 03101647 A2 | 12/2003 |
| WO | WO 2005009489 A2 | 2/2005 |
| WO | WO 2005009729 A2 | 2/2005 |
| WO | WO 2006014294 A1 | 2/2006 |
| WO | WO 2006130350 A2 | 12/2006 |
| WO | WO 2008048820 A2 | 4/2008 |
| WO | WO 2008048820 A3 | 7/2008 |
| WO | WO 2008100784 A2 | 8/2008 |
| WO | WO 2009046212 A2 | 4/2009 |
| WO | WO 2009128943 A2 | 10/2009 |
| WO | WO 2010056962 A1 | 5/2010 |
| WO | WO 2010056962 A8 | 7/2010 |

OTHER PUBLICATIONS

Restoration® Modular Revision Hip System, Product. Reference Guide for Cone/Conical and Broached/Fluted & Plasma Implants and Instruments, brochure, 2004 St ker, a es 1-12.*

The Effects of Conformity and Load in Total Knee Replacement, Kuster, et al, Clinical Orthopaedics and Related Research, No. 375, Jun. 2000.

Effects of Coronal Plane Conformity on Tibial Loading in TKA: A Comparison of AGC Flat Versus Conforming Articulations, Brent, et al, Orthopaedic Surgery, Surgical Technology International, XVIII.

ASTM Standard D4518-91, "Standard Test Methods for Measuring Static Friction of Coating Surfaces," ASTM International, West Conshohocken, PA, 1991 DOI: 10.1520-D4518-91, www.astm.org., 5 pages.

ASTM Standard E9-89a(2000), "Standard Test Methods of Compression Testing of Metallic Materials at Room Temperature," ASTM International, West Conshohocken, PA, 2000 DOI: 10.1520-E0009-89AR00, www.astm.org, 9 pages.

ASTM Standard F1580-01, "Standard Specification for Titanium and Titanium-6 Aluminum-4 Vanadium Alloy Powders for Coatings of Surgical Implants," ASTM International, West Conshohocken, PA, 2001 DOI: 10.1520-F1580-01, www.astm.org, 4 pages.

(56) References Cited

OTHER PUBLICATIONS

International Organization for Standardization, "ISO 3274:1996," 1996, 20 pages.
International Organization for Standardization, "ISO 4287:1997," 1997, 36 pages.
Alconox, Inc., "Liquinox Technical Bulletin," 2006 , 2 pages.
Biomet, Vanguard® Mono-Lock™ Tibial System, Patented Convertible Tibial Bearing Technology, 2009, 2 Pages.
C.E. Wen et al., "Novel Titanium Foam for Bone Tissue Engineering," Journal of Materials Research, vol. 17, No. 10, pp. 2633-2639, 7 pages.
Carl Zeiss, Zeiss Surfcomm 5000—"Contour and Surface Measuring Machines," 2005, 16 pages.
DePuy Inc., "AMK Total Knee System Product Brochure", 1996, 8 pages.
DePuy Knees International, "Sigma CR Porocoat®," 1 page.
DePuy Orthopaedics, Inc., "AMK Total Knee System Legend II Surgical Technique", 1998, 30 pages.
Depuy PFC Sigma RP, "PFC Sigma Knee System with Rotating Platform Technical Monograph", 1999, 0611-29-050 (Rev. 3), 70 Pages.
General Plastics Manufacturing Company, "LAST-A-FOAM@ Products Guide to Tooling Applications, Bonding, Filling and Sealing," FR-6700 Tooling Apps Product Sheet, 2010, 16 pages.
General Plastics Manufacturing Company, "LAST-A-FOAM@," FR-6700 Series Product Sheet, 2000, 6 pages.
General Plastics Manufacturing Company, "Tooling Board Specifications," FR-4500® Series Specification Sheet, 2002, 2 pages.
General Plastics Manufacturing Company, "Tooling Boards," FR-4500® Series Product Data Sheet, 2002, 4 pages.
Johnson & Johnson Orthopaedics, "Primary Cruciate-Retaining & Cruciate-Substituting Procedure," Reference Guide for Use with P.F.C. Sigma Knee Systems, 1998, 8 pages.
Maca, et al., "Electrophorectic Deposition of Alumina and Zirconia I. Single-Component Systems", Ceramics International, vol. 20, pp. 843-852.
Media Cybernetics, Inc., "Image-Pro Plus: Powerful and Customizable Image Processing and Analysis Software for Industrial Applications," 2009, 8 pages.
Micro Powders, Inc., "Technical Data Sheet—Propyltex Waxes," 1999, 1 page.
Phelly Materials, Inc., "Hydride and dehydride CP Ti and Ti—6Al—4V Powders," 2007, 1 page.
Phelly Materials, Inc., "Pure Metal Powder," 2007, 1 page.
DePuy Orthopaedics, Inc., "Sigma Fixed Bearing Knees—Function with Wear Resistance", 2010, 0612-65-508 (Rev. 1), 20 pages.
Signus Medizintechnik, "PEEK-OPTIMA®, The Polymer for Implants, Technical Information for the Medical Professional", 7 pages.
Kinbrum, A., "Taking a Peek at Material Options for Orthopedics," Advantage Business Media, 2008, 6 pages.
Zimmer Nexgen Trabecular Metal Tibial Tray, The Best Thing Next to Bone, 97-5954-001-00, 2007, 4 Pages.
Zimmer, Trabecular Metal Monoblock Tibial Components, An Optimal Combination of Material and Design, www.zimmer.com, 2009, 3 pages.
Zimmer, Trabecular Metal™ Technology, www.zimmer.com, 2009, 4 pages.

European Search Report for European Patent Application No. 08164944.4-2310-2042131, Mar. 16, 2009, 12 pgs.
European Search Report for European Patent Application No. 08253140.1-2310, Dec. 23, 2008, 8 pgs.
Specification As Filed in U.S. Appl. No. 12/691,280, filed Jan. 21, 2010, 35 Pages (Including Drawings).
IDS for U.S. Appl. No. 12/691,280, Submitted on Jan. 21, 2010, 57 Pages.
Non-Final Office Action in U.S. Appl. No. 12/691,280, Dated Mar. 29, 2011, 10 Pages.
Specificiation As Filed in U.S. Appl. No. 12/894,651, filed Sep. 30, 2010, 29 Pages (Including Drawings).
European Search Report From Corresponding EPO Search Report, EPO Application No. 11150577.2-2310, Dated Apr. 16, 2011, 9 Pages.
Coordinate Ultra Revision Knee System, Surgical Technique, Depuy, A Johnson & Johnson Company, 24 Pages, 1.5M1102, 0601-82-000 (Rev. 3), 1997.
PFC Sigma RP-F Product Rationale, Depuy, A Johnson & Johnson Company, 12 Pages, 3M0106, 0612-27-503, 2006.
LCS Complete, LCS RPS Flexion Product Rationale, Depuy, A Johnson & Johnson Company, 24 Pages, Cat. No. 9075-16-000, Ver. 1, 2008.
What Design Factors Influence Wear Behavior in Total Knee Replacement? American Academy of Orthopaedic Surgeons, pp. 156-169, Material & Design Considerations—Implant Wear in Total Joint Replacement, 2001.
Galvin, A., et al, "The Influence of Tibial Tray Design on the Wear of Fixed-Bearing Total Knee Replacements", Proc. IMECHE vol. 222, Part H: J. Engineering in Medicine, pp. 1289-1293, 2008.
Jayabalan, Prakash et al., "Backside Wear in Modern Total Knee Designs", HSSJ (2007) 3: 30-34, DOI 10.1007/S11420-006-9033-0, Published Online: Dec. 14, 2006—Hospital for Special Surgery 2006.
APEX Knee System, Exhibit A 510(K) Summary, K060192, Submitter: Omni Life Science, Inc., 5 Pages, 2006.
Akisue, Toshihiro, M.D., et al, "Backside" Polyethylene Deformation in Total Knee Arthroplasty, The Journal of Arthroplasty, vol. 18, No. 6, pp. 784-791, 2003.
Parks, Nancy L., M.S., et al., The Coventry Award, "Modular Tibial Insert Micromotion, A Concern With Contemporary Knee Implants", pp. 10-15, Clinical Orthopaedics and Related Research, No. 356, Nov. 1998.
Azzam, Michael G., M.D., et al, Second-Generation Locking Mechanisms and Ethylene Oxide Sterilization Reduce Tibial Insert Backside Damage in Total Knee Arthroplasty, The Journal of Arthroplasty vol. 26, No. 4, pp. 523-530, 2011.
Kuster, et al "The Effects of Conformity and Load in Total Knee Replacement", Clinical Orthopaedics and Related Research, No. 375, pp. 302-312 (2000) 11 Pgs.
Berend, et al "Effects of Coronal Plane Conformity on Tibial Loading in TKA: A Comparison of AGC Flat Versus Conforming Articulations", Orthopaedic Surgery, Surgical Technology International XVIII, pp. 207-212 (2009) 6 Pgs.
European Search Report for Corresponding EPO Patent App. No. 11150577.2-2310, Dated Apr. 26, 2011 (9 pages).
Japanese Notification of Reasons for Refusal for Patent Application No. 2011-009548 Dated Oct. 27, 2014 With a Mail Date of Nov. 4, 2014, 4 Pages.

\* cited by examiner

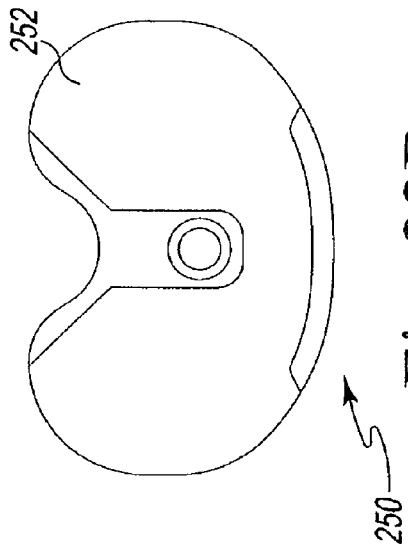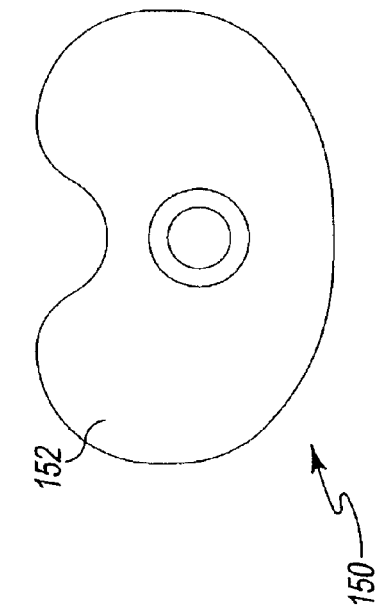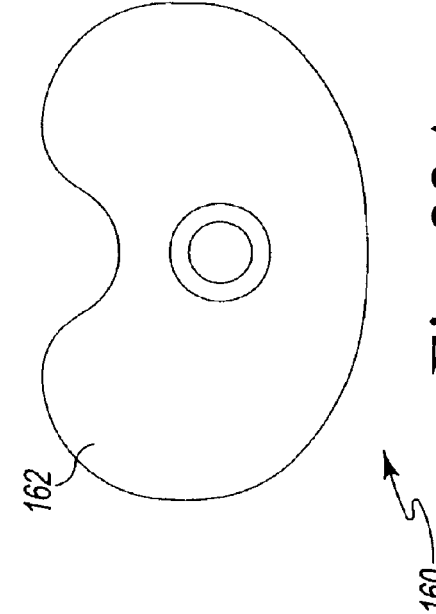
Fig. 22B
Fig. 23B
Fig. 22A
Fig. 23A

KNEE PROSTHESIS SYSTEM

BACKGROUND

This disclosure relates generally to surgical devices and procedures, and more particularly, to implantable, total knee replacement prostheses.

The most widely-used type of knee prosthesis for implantation into a patient during a total knee replacement (TKR) procedure includes three components: a metallic, femoral component that attaches to the distal femur; a metallic, tibial component (or tray) that attaches to the proximal tibia; and a polymeric (UHMWPE), insert (also called a bearing or an inlay) that fits between the femoral and tibial components. Various types of patella replacements are also available for use in combination with some of these knee prostheses. Two types of knee prostheses are a posterior-stabilized (PS) prosthesis, for when the posterior cruciate ligament is no longer viable, and a (posterior) cruciate-retaining (CR) knee prosthesis. Each of these two types of knee prostheses may be provided as a fixed bearing knee prosthesis, in which the insert does not move relative to the tibial component, or a mobile bearing knee prosthesis, in which the insert rotates upon a smooth platform of the tibial component. Whether to use a mobile insert or a fixed insert depends largely on the condition of the patient's knee ligaments and other soft tissues.

A knee prosthesis system may include numerous sizes of femoral, tibial and insert components to accommodate the variation of patient anatomies in the worldwide TKR patient population. The design of a knee prosthesis system requires trade-offs among many important factors related to kinematic performance, clinical outcomes, implant longevity, cost, and ease of use, to name just a few. An important consideration relative to both the kinematic performance and the life of the knee prosthesis is the degree of conformity between the femoral component bearing surfaces and the insert bearing surfaces.

Investigators typically characterize conformity in either the coronal plane or sagittal plane as the ratio of the convex radius of a femoral condyle of the femoral component to the concave radius of the interfacing insert surface. A conformity ratio of zero represents a flat insert surface, corresponding to very high contact stress at high loads. A conformity ratio of 0.99 represents high conformity, corresponding, in general, to high contact area, relatively low contact stress and, subsequently, reduced wear rate of the polyethylene surface of the insert.

Investigators have found that conformity in the coronal plane may affect prosthesis life more than conformity in the sagittal plane. For example, in an article by Kuster, et al, "The effects of conformity and load in total knee replacement" (*Clinical Orthopaedics and Related Research*, Number 375, pp. 302-12, June 2000), the authors found that the compressive surface stress, the shear stress and the von Mises stress were affected by changes to the conformity ratio and to a lesser extent by load changes. In a more recent article by Berend, et al, "Effects of coronal plane conformity on tibial loading in TKA: a comparison of AGC flat versus conforming articulations" (*Surgical Technology Int.*, Number 18, pp. 207-212, 2009), the authors studied the effect of conformity on loading of the proximal tibia of the patient. Improper loading of the proximal tibia may lead to aseptic loosening of the tibial component in the tibia and eventually prosthesis failure requiring revision surgery. The authors found that coronally dished components created a strain increase in the anterior medial tibia while creating a significant strain decrease in the posterior tibia. They also found that proximal tibial strains were decreased and centralized in conforming versus flat articulations.

It is known in the art, however, that very high conformity may also lead, for example, to undesirable loading conditions on the insert surface or to excessive constraint of the femoral component, thereby inhibiting joint motions important to joint performance and patient comfort. Therefore, designs with intermediate values of contact area may be optimal as long as the stresses are below the yield strength of the insert material, in order to provide the optimal combination of joint laxity and conformity.

Complicating the challenge faced by knee prosthesis designers is the variability of patient anatomies in the worldwide, TKR patient population. Smaller patients with smaller femurs require, obviously, smaller knee prostheses. Each of the medial and lateral condyles of a femoral component of a small femoral component has a smaller coronal radius than a large femoral component for a large patient. To maintain the appropriate comformity ratio, as well as other geometrical relationships including condylar spacing, the small femoral component must be matched to a properly sized insert. In addition to the wide range of patient sizes, however, the dimensional proportionality between the femur and tibia bones also varies widely. For example, some patients, have a larger distal femur than other patients for a given size of the proximal tibia. In such cases when using currently available knee prosthesis systems, the surgeon may need to choose to implant a femoral component that is slightly mismatched with the femur and matched with the insert, or a femoral component that is matched with the femur and slightly mismatched with the insert.

Therefore, in view of the foregoing considerations, there is a need for a knee prosthesis system that allows the surgeon to select a femoral component that is sized to fit the femur of a particular patient, a tibial component that is sized to fit the tibia, and an insert that optimally matches the femoral component and is compatible with the tibial component. Such a knee prosthesis system should include both fixed and mobile types of prostheses and provide for both CR and PS procedures. Furthermore, the system should accommodate the wide variety of patient anatomies in the worldwide population.

In addition to providing optimally matched knee prosthesis components, there is an ongoing need to maintain or lower the costs and complexity of knee prosthesis systems. A knee prosthesis system may include femoral, tibial and insert components in a number of sizes, for each of the right and left knees, to accommodate variations in patient anatomies and conditions. In addition, each of inserts may be provided in a number of thicknesses so that the surgeon may select the one that results in the appropriate joint tension. Consequently, knee prosthesis manufacturers must provide a very large inventory of components representing a large number of different size combinations to accommodate the worldwide patient population. What is needed, therefore, is an improved, knee prosthesis system that allows component interchangeability to provide the necessary size combinations with a minimal number of components.

Another consideration during the design of knee prosthesis systems is bone preparation for implantation of the PS femoral component. Both the PS and the CR femoral components have a pair of spaced-apart condyles that are somewhat similar to the natural condyles of the distal femur. For the PS femoral component, a box (or intracondylar notch) positioned between the condyles includes features for interaction with a spine on the PS insert. Implantation of the PS femoral component requires cutting a recess into the distal femur to receive the box. In some current, knee prosthesis systems, the size of the box is the same for all of the PS femoral component sizes, thereby requiring cutting the same size recess into the distal femur, even for smaller femurs. It is desirable, however, to conserve natural bone, if possible, during preparation of the femur for attachment of the femoral component. There is a further need, therefore, for a knee prosthesis system in which each of the PS femoral components has a box that is sized proportionately to the femur size, while also addressing the previously described needs.

Yet another consideration during the design of knee prosthesis systems is bone preparation for implantation of the tibial component. Currently available, mobile and fixed TKR prosthesis systems include tibial components for a range of anatomical sizes. For some of these systems, the tibial component for a mobile TKR prosthesis of a particular size has a different configuration than that of a fixed TKR prosthesis of the same size. Specifically, the platform that supports the fixed bearing insert may have a different shape than the platform that supports the mobile bearing insert. This may result in a small, but possibly significant, difference in coverage of the resected, tibial plateau surface. Although less than ideal, one way surgeons may obtain the desired, tibial bone coverage is to select a larger size tibial component. What is more desirable is a TKR system that has mobile and fixed tibial components with a common platform profile shape that is optimized for interaction with surrounding tissues, kinematic performance, etc.

Also, currently available TKR systems have tibial components with stems of variable lengths to accommodate different tibial bone conditions. Furthermore, the stems for mobile tibial components may have a different configuration than the stems for fixed tibial components. Subsequently, such systems require that a number of different reaming instruments be available for each surgical procedure. A preferable TKR system would have mobile and fixed tibial components with stems of different lengths, but not requiring several different reaming instruments for preparing the tibia. This would also provide the surgeon with the intraoperative flexibility to select the appropriate type of tibial component, while reducing the number of instruments that would need to be available during the surgical procedure.

BRIEF DESCRIPTION OF FIGURES

While this specification concludes with claims that particularly point out and distinctly claim the invention, the following description and the accompanying figures further illustrate some non-limiting examples of the claimed invention. Unless otherwise indicated, like reference numerals identify the same elements.

FIG. 22A is a superior view of the size one, mobile tibial component of FIG. 18.

FIG. 22B is a superior view of a size one, fixed tibial component.

FIG. 23A is a superior view of the size three, mobile tibial component of FIG. 19.

FIG. 23B is a superior view of a size three, fixed tibial component.

DETAILED DESCRIPTION

Figure 1:
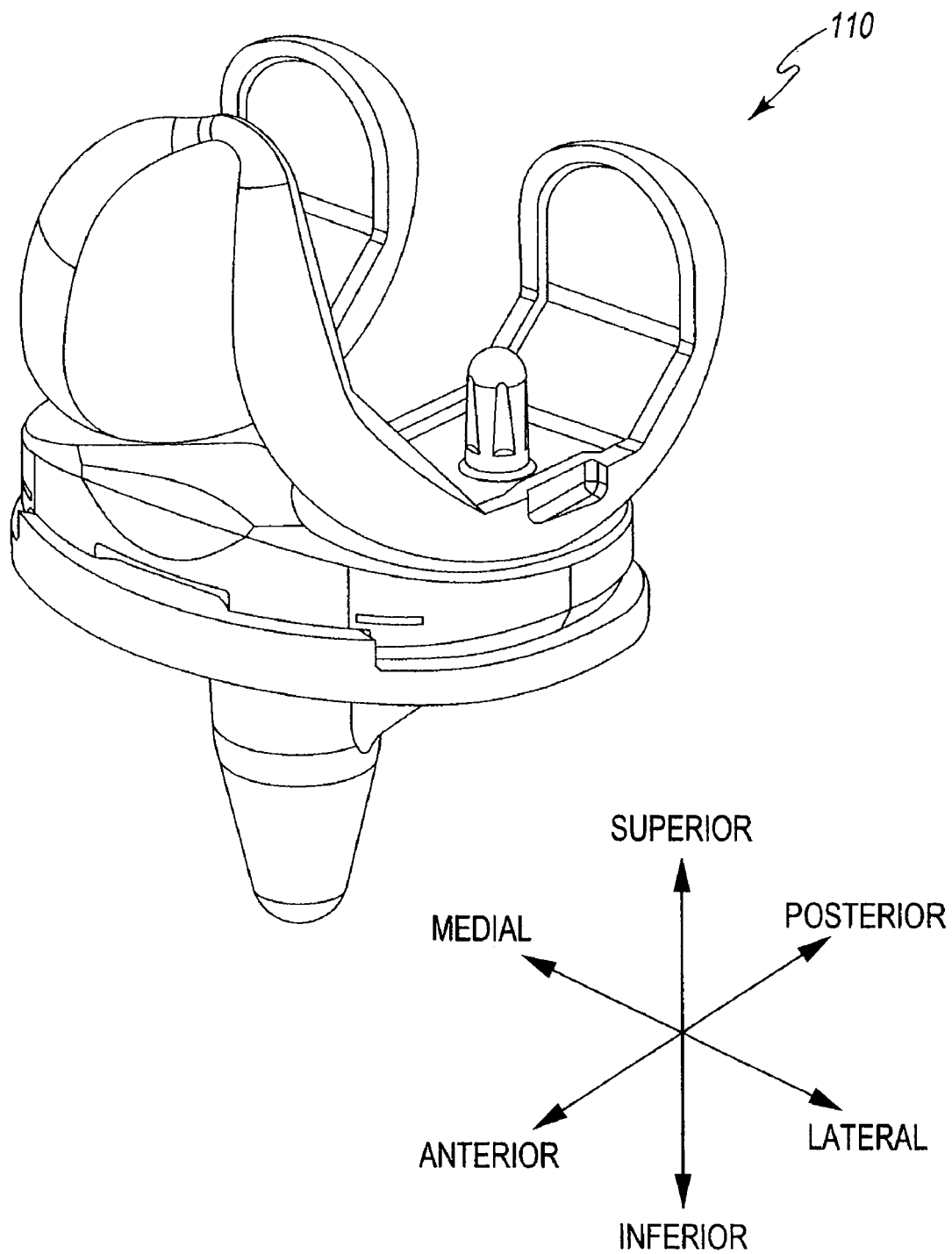
FIG. 1 is a perspective view of a fixed CR prosthesis 110.
Figure 2:
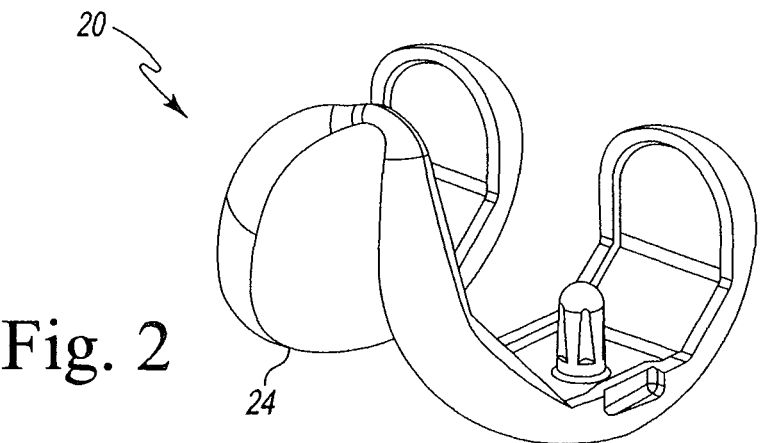
FIG. 2 is a perspective view of a CR femoral component 20, which is part of fixed CR prosthesis 110 shown in FIG. 1 and mobile CR prosthesis 130 shown in FIG. 9.
Figure 3:
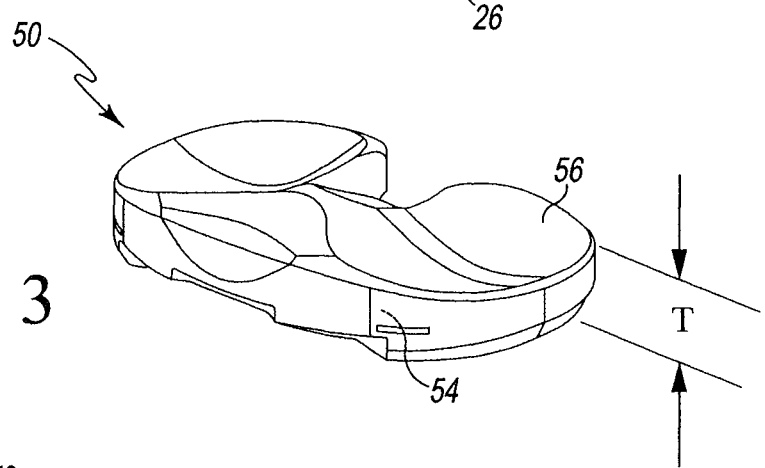
FIG. 3 is a perspective view of a fixed CR insert 50, which is part of fixed CR prosthesis 110 shown in FIG. 1.

In this disclosure, the terms "anterior, posterior, lateral, medial" generally refer to the front, back, outside and midline of the surgical patient, respectively, although we also use these terms in reference to the devices. FIG. 1 shows directional arrows for these terms and the terms "inferior, superior". Also, we intend references to "surgeon" and "user" to include also any person who may assist the surgeon during the surgical procedure.

The following are incorporated herein by reference in their entirety:

U.S. Pat. No. 7,628,818, titled "Fixed-Bearing Knee Prosthesis Having Interchangeable Components", filed on Sep. 28, 2007 by Hazebrouck, et al, (hereinafter "Hazebrouck") and published on Apr. 2, 2009.

U.S. patent application Ser. No. 12/165,582, titled "Posterior-Stabilized Orthopaedic Prosthesis", filed on Jun. 30, 2008 by Wyss, et al, (hereinafter "Wyss").

Hazebrouck discloses a fixed bearing, knee prosthesis system in which each of differently sized inserts are compatible with each size of tibial component, so that it is possible for a surgeon to select a tibial component that is properly sized for a patient's tibia, and an insert that is matched with the femoral component.

Hazebrouck also discloses that the femoral components have medial condyle surfaces and lateral condyle surfaces and that the bearing inserts have upper surfaces including medial and lateral bearing surfaces. Each medial bearing surface is configured to articulate with the medial condyle surface of a femoral component, and each lateral bearing surface is configured to articulate with the lateral condyle surface of a femoral component. Lower surfaces of the fixed bearing inserts have recesses defined therein to receive posterior and anterior buttresses of the fixed tibial components. Each of the plurality of bearings also includes a pair of posterior tabs arranged to be respectively received in the undercuts defined in the pair of arms of the posterior buttress.

Hazebrouck also discloses that the fixed bearing inserts may be made of a polymeric material such as ultrahigh molecular weight polyethylene (UHMWPE) and that the bearing inserts may be of different sizes, particularly different widths. However, each of such differently-sized bearing inserts may include mating features that are commonly-sized and commonly-located with the commonly-sized and commonly-located features of the fixed tibial components. In particular, each of the fixed bearing inserts across a range of different sizes may include posterior and anterior recesses that are positioned and sized to tightly fit against the edges of the buttresses of components differently-sized tibial components.

Wyss discloses a knee prosthesis system having a plurality of distinctly-sized PS inserts (fixed or mobile) having a spine extending superiorly from an inferior surface. The spine has a posterior side that has a concave cam surface and a convex cam surface. Each of the PS femoral components has a pair of spaced-apart condyles defining an intracondylar notch that has a posterior cam. The posterior cam includes a concave cam surface and a convex cam surface. The concave cam surface of the posterior cam contacts the convex cam surface of the spine during a first range of flexion and the convex cam surface of the posterior cam contacts the concave cam surface of the spine during a second range of flexion.

Figure 16:
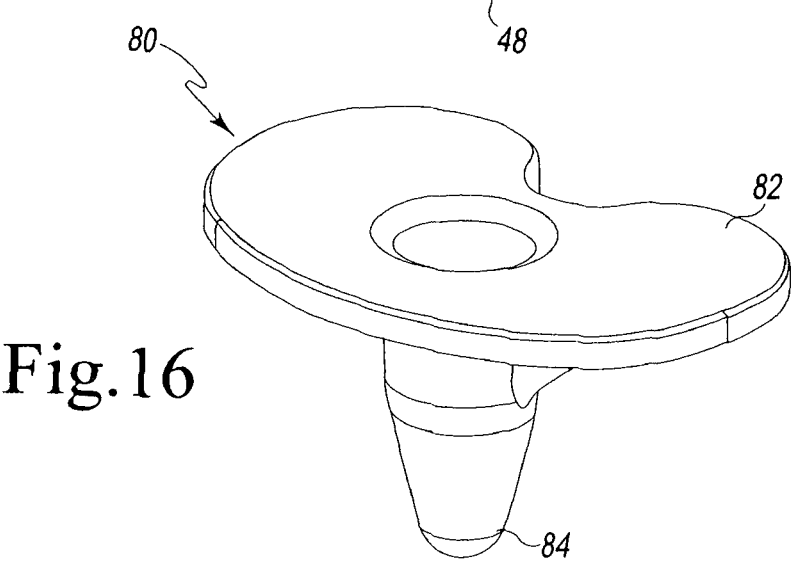
FIG. 16 is a perspective view of mobile tibial component 80, which is also shown in FIG. 12.
Figure 17:
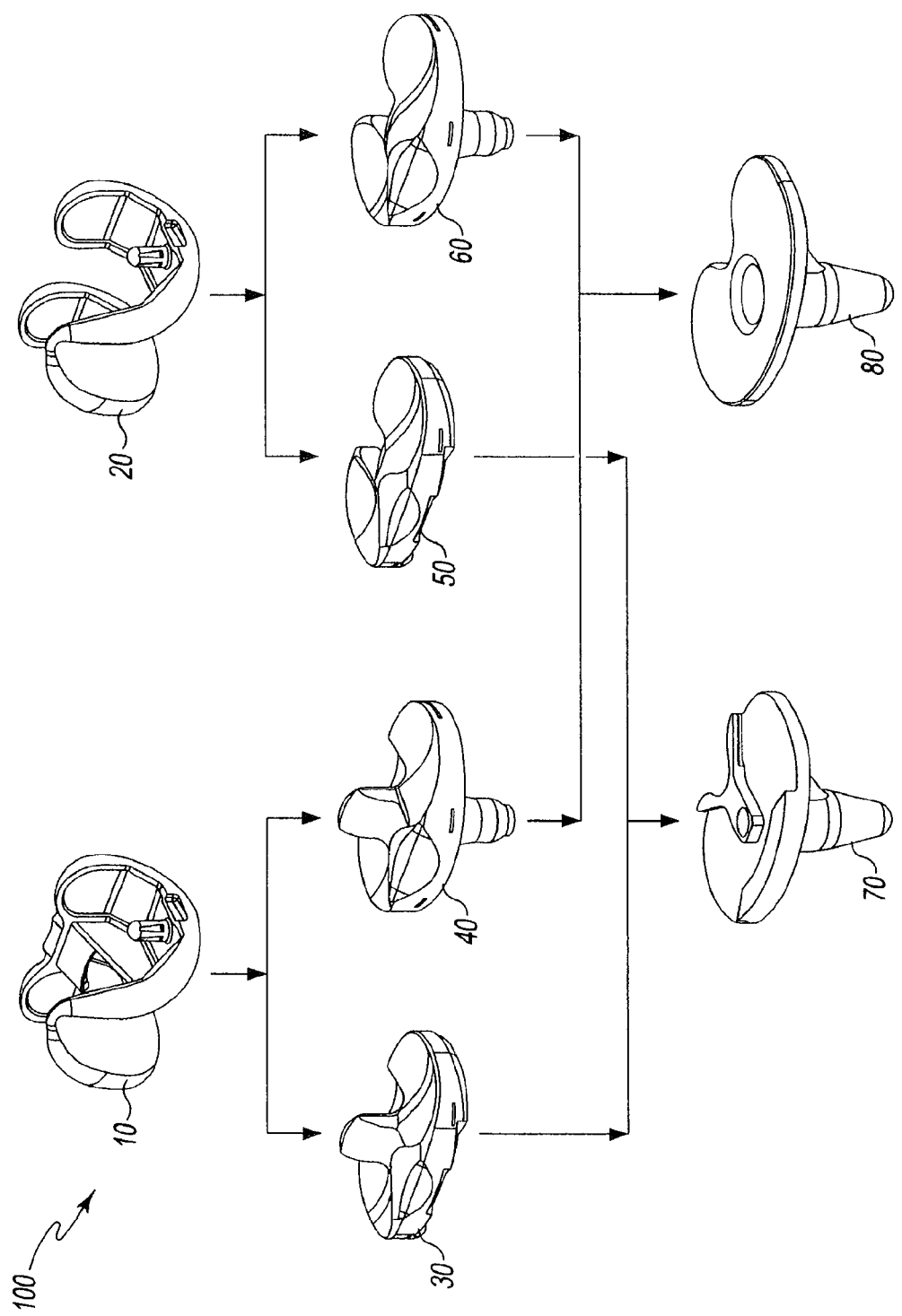
FIG. 17 is a chart representing knee prosthesis system 100 for configuring, in a plurality of size combinations, each of the prostheses shown in FIGS. 1, 5, 9 and 13.

FIGS. 1-16 show components of a knee prosthesis system 100 that is shown in FIG. 17. Each of these components may be provided in a plurality of sizes and may be matched together as described next, thereby providing the surgeon with a large plurality of size combinations. Using knee prosthesis system 100, the surgeon may select, for each patient in a large patient population, a size combination that correctly matches both the femur and the tibia of the patient. That is, the femoral component is distinctly-sized to fit the femur and the tibial component is distinctly-sized to fit the tibia, and the components of the knee prosthesis are optimally match to avoid compromising joint performance.

One characteristic of the distinctly-sized femoral and tibial components of knee prosthesis system 100 is proportionality of each component to the particular size of bone to which the component is to be attached. In general, the dimensional scale of the component varies, but not the shape. For example, the femoral component may have a proportionally-sized, intercondylar distance, such that a large femoral component has a proportionally longer intercondylar distance than that of a small femoral component. Similarly, a large tibial component may have a proportionally wider and deeper, posterior notch than that of a small tibial component.

Figure 4:
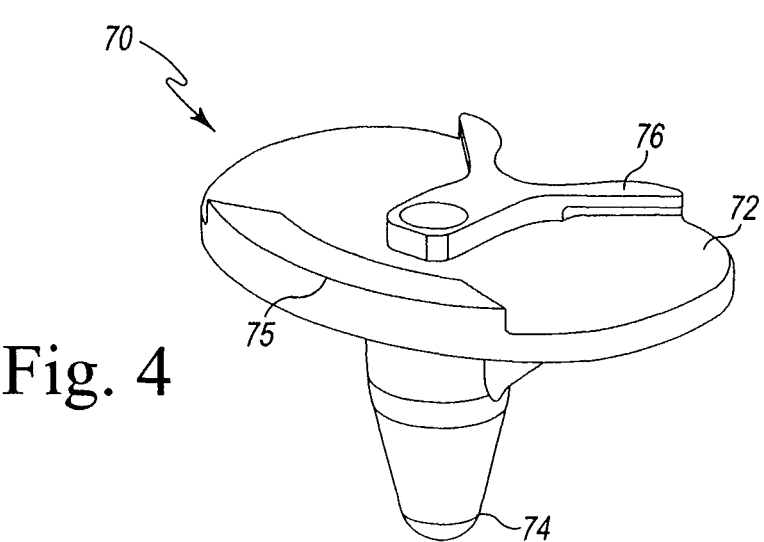
FIG. 4 is a perspective view of a fixed tibial component 70, which is part of fixed CR prosthesis 110 shown in FIG. 1 and a fixed PS prosthesis 120 shown in FIG. 5.
Figure 8:
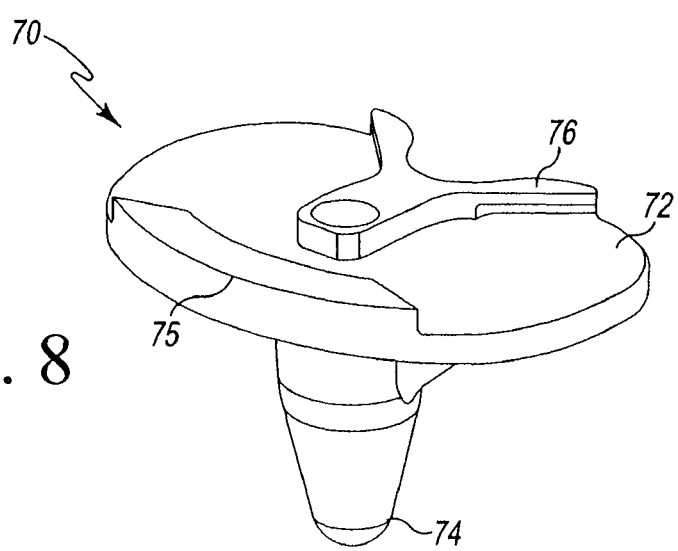
FIG. 8 is a perspective view of fixed tibial component 70, which is also shown in FIG. 4.

FIG. 1 is a perspective view of a cruciate-retaining, fixed bearing, knee prosthesis 110, also referred to as a fixed CR prosthesis 110, which includes a CR femoral component 20 (FIGS. 2 and 10), a fixed CR insert 50 (FIG. 3) and a fixed tibial component 70 (FIGS. 4 and 8). Fixed CR prosthesis 110 may be identical to or similar to the knee prosthesis shown in FIG. 1 of Hazebrouck. As disclosed in Hazebrouck, any one of a plurality of differently-sized inserts (or bearings) may be secured to any one of a plurality of differently-sized tibial components (or trays). As a result, articulation surface geometries and other features of the insert may be enhanced for each size of femoral component. Such interchangeability also allows for smaller size increments in the design of a range of femoral components. CR femoral component 20 includes a medial condyle 24 and a lateral condyle 26, both of which articulate upon a superior surface 56 of fixed CR bearing 50. An anterior buttress 75 and a posterior buttress 76 of fixed tibial component 70 (see FIG. 4) fixedly retain CR insert 50 to fixed tibial component 70, such that an inferior surface 54 of CR insert 50 rests on a platform 72 of fixed tibial component 70. These mounting features are commonly-sized and commonly-located across different sizes of fixed tibial components 70. Fixed tibial component 70 also includes a stem 74 that inserts into the surgically prepared proximal tibia. Fixed CR insert 50 may be provided in any of a plurality of thicknesses, designated as "T" in FIG. 3.

Figure 5:
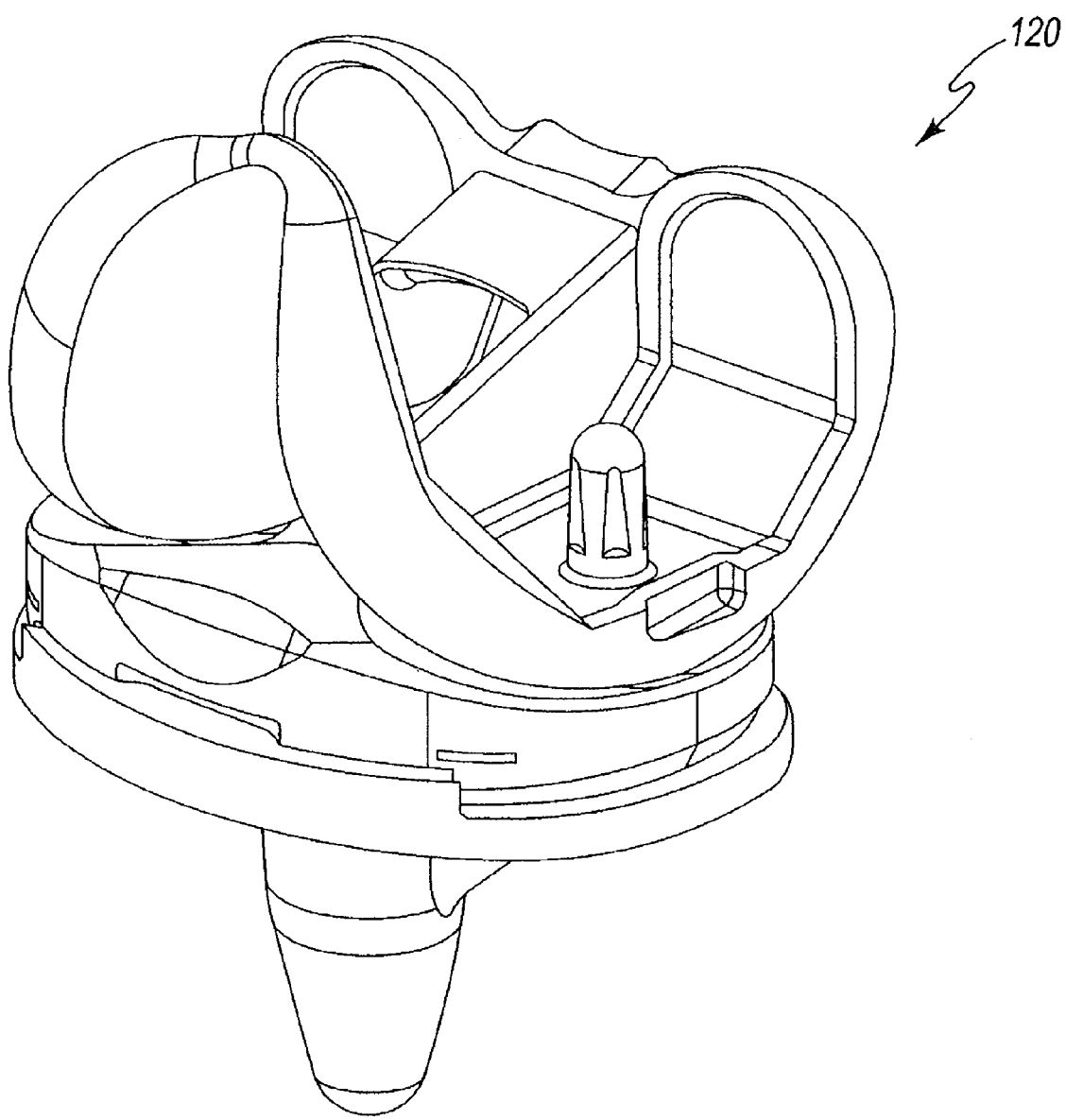
FIG. 5 is a perspective view of fixed PS prosthesis 120.
Figure 6:
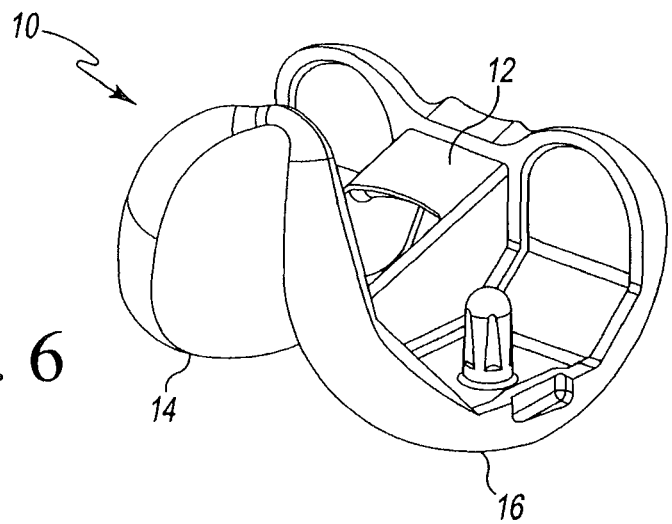
FIG. 6 is a perspective view of a PS femoral component 10, which is part of fixed PS prosthesis 120 shown in FIG. 5 and a mobile PS prosthesis 140 shown in FIG. 13.
Figure 7:
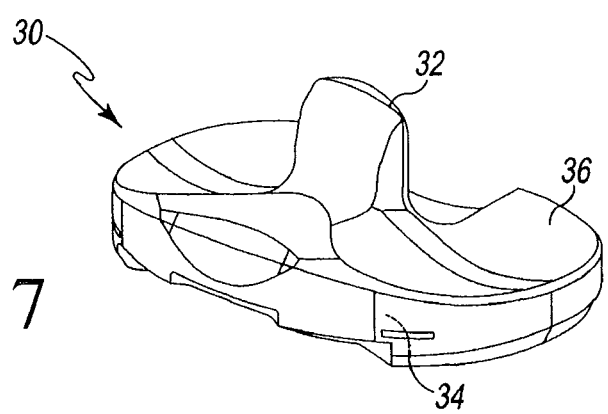
FIG. 7 is a perspective view of a fixed PS insert 30, which is part of fixed PS prosthesis 120 shown in FIG. 5.

FIG. 5 is a perspective view of a posterior-stabilized, fixed bearing, knee prosthesis 120, also referred to as a fixed PS prosthesis 120, which includes a PS femoral component 10 (FIG. 6), a fixed PS insert 30 (FIG. 7) and fixed tibial component 70 (FIGS. 4 and 8). PS femoral component 10 may be identical to or similar to the femoral component shown in FIG. 1 of Wyss. PS femoral component 10 includes a medial condyle 14 and a lateral condyle 16, both of which articulate upon a superior surface 36 of fixed PS insert 30. PS femoral component 10 also includes a box 32 positioned between medial condyle 14 and lateral condyle 16. Box 32 encases a posterior cam and an anterior cam (both hidden) that operationally engage with a spine 32 of fixed PS insert 30 as described in Wyss. Anterior buttress 75 and posterior buttress 76 of fixed tibial component 70 (see FIGS. 4 and 8) retain PS insert 30, such that an inferior surface 34 of PS insert 30 rests on a platform 72 of fixed tibial component 70.

Figure 9:
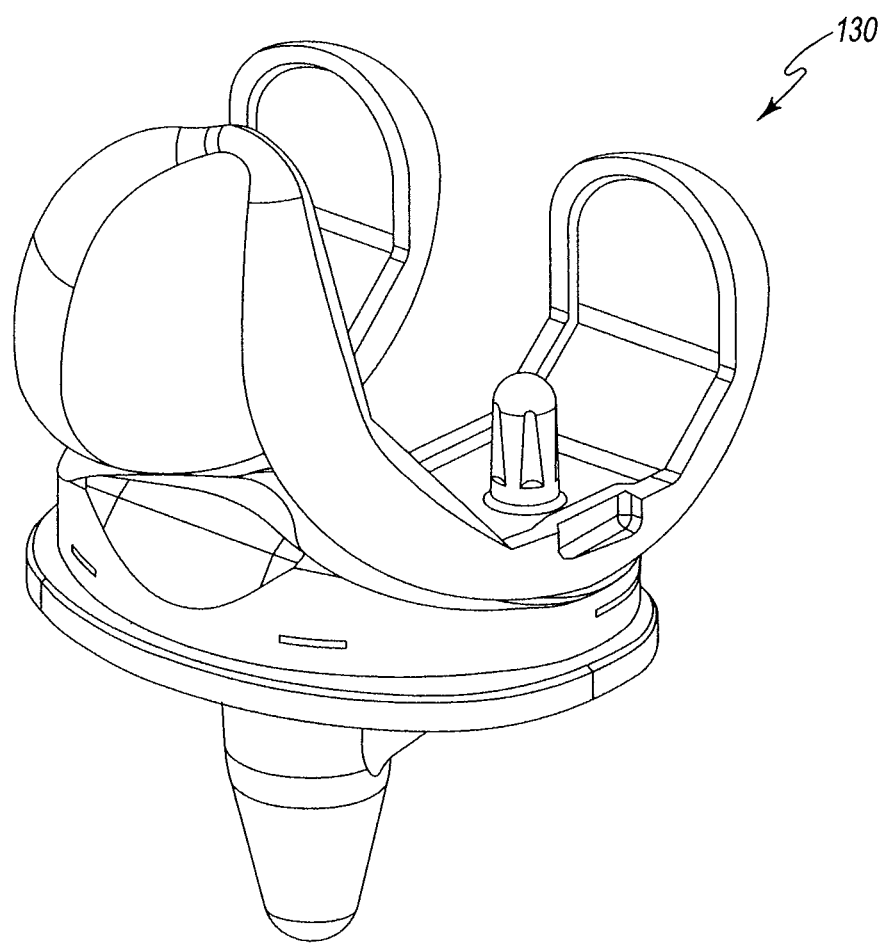
FIG. 9 is a perspective view of a mobile CR prosthesis 130.
Figure 10:
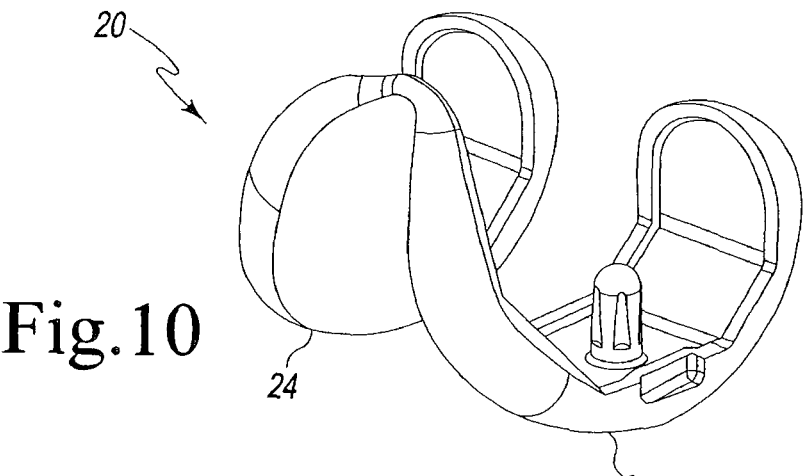
FIG. 10 is a perspective view of CR femoral component 20, which is also shown in FIG. 2.
Figure 11:
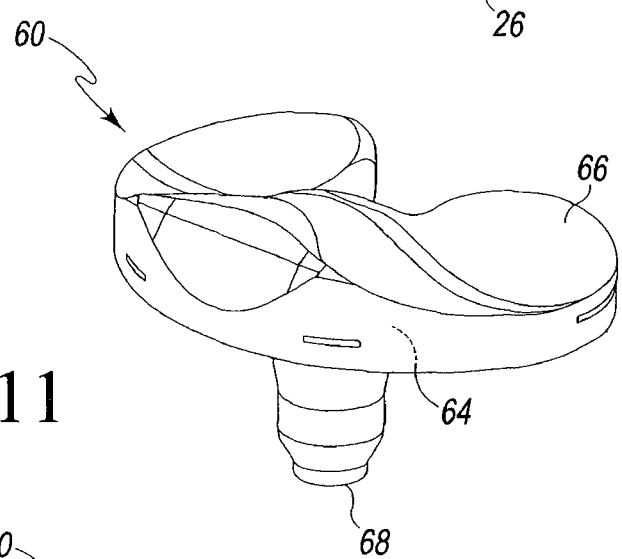
FIG. 11 is a perspective view of a mobile CR insert 60, which is part of mobile CR prosthesis 130 shown in FIG. 9.

FIG. 9 is a perspective view of a cruciate-retaining, mobile bearing, knee prosthesis 130, also referred to as a mobile CR prosthesis 130, which includes CR femoral component 20 (previously described for FIG. 2), a mobile CR bearing insert 60 and a mobile tibial component 80. Medial condyle 24 and lateral condyle 26 of CR femoral component 20 articulate on a superior surface 66 of mobile CR insert 60. An inferior surface 64 of mobile CR insert 60 articulates against platform 82 of mobile tibial component 80. A post 68 extends inferiorly from inferior surface 64 and rotatably inserts into a hollow stem 84 of mobile tibial component 80.

Figure 12:
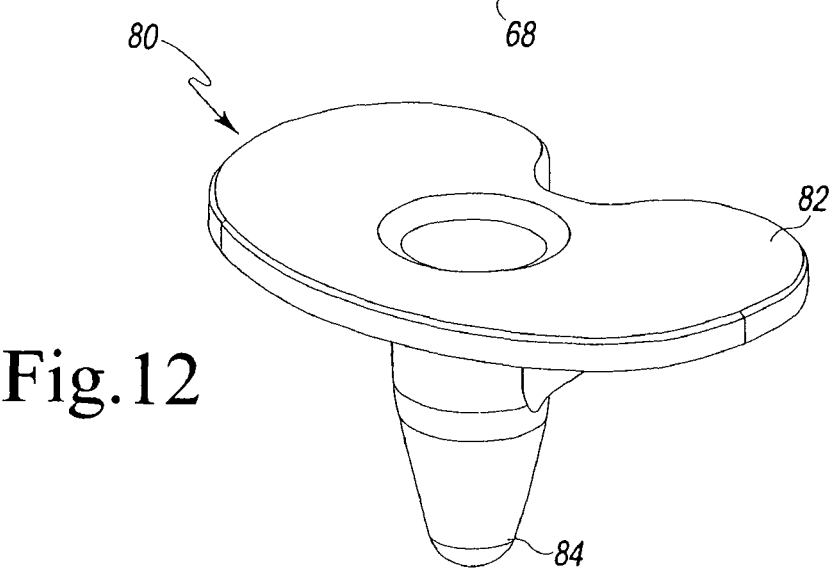
FIG. 12 is a perspective view of a mobile tibial component 80, which is part of mobile CR prosthesis 130 and a mobile PS prosthesis 140 shown in FIG. 13.
Figure 13:
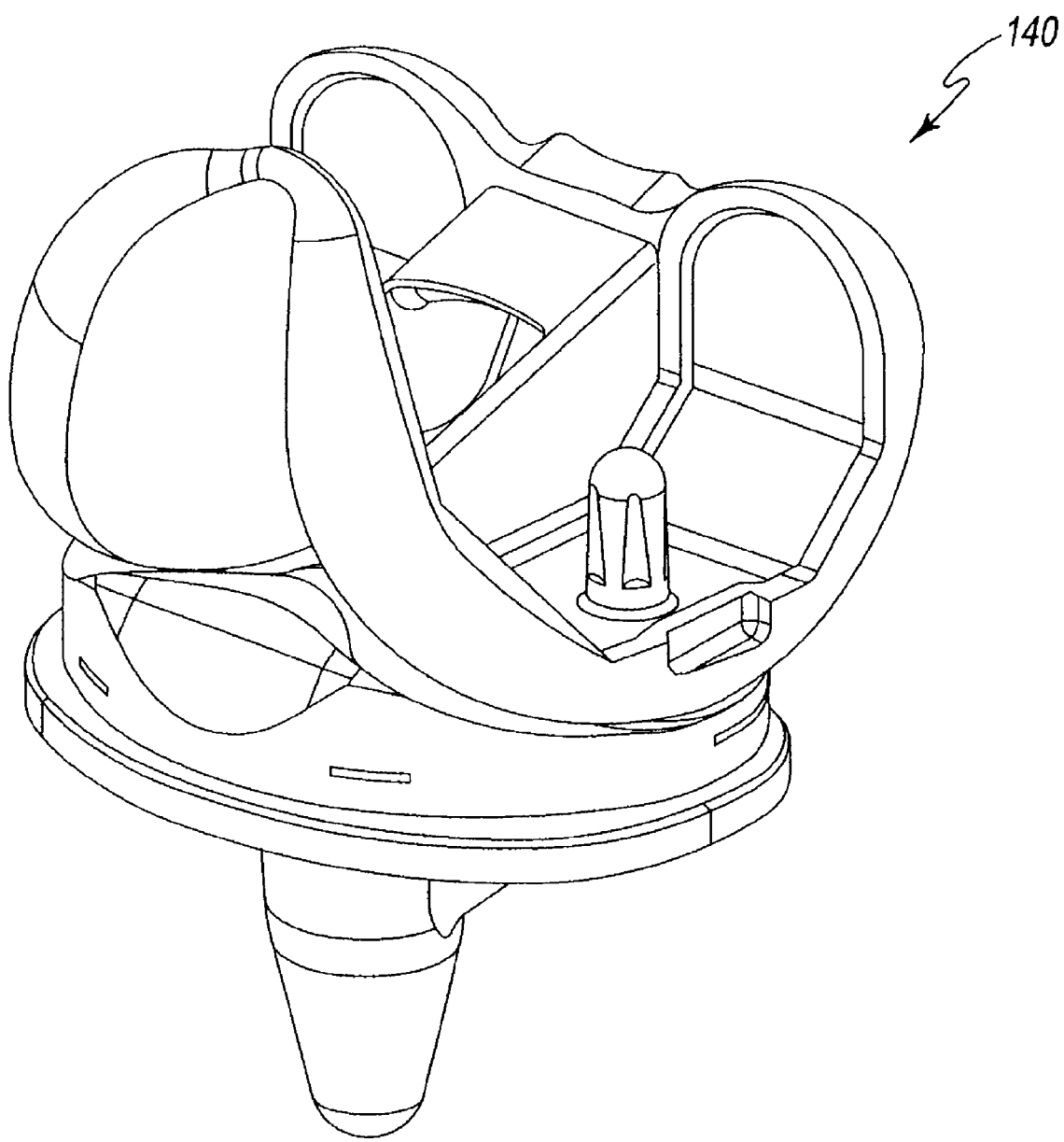
FIG. 13 is a perspective view of mobile PS prosthesis 140.
Figure 14:
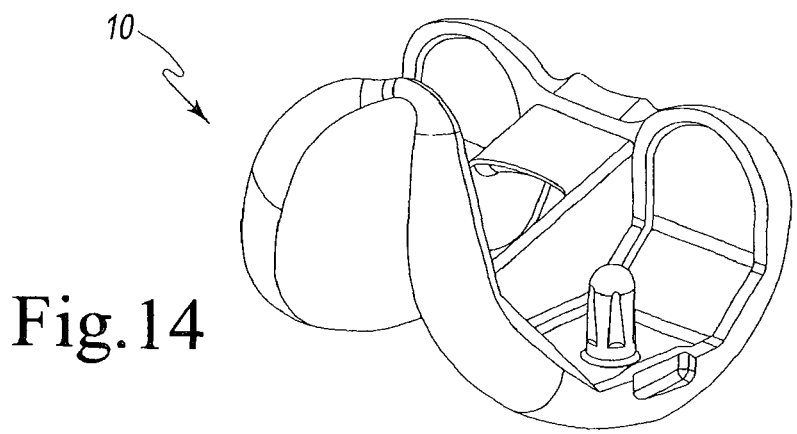
FIG. 14 is a perspective view of PS femoral component 10, which is also shown in FIG. 10.
Figure 15:
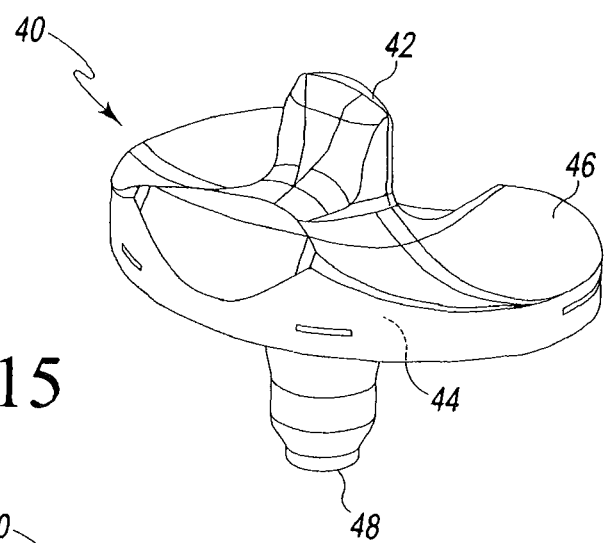
FIG. 15 is a perspective view of a mobile PS insert 40, which is part of mobile PS prosthesis 140 shown in FIG. 13.

FIG. 13 is a perspective view of a posterior-stabilized, mobile bearing, knee prosthesis 140, also referred to as a mobile PS prosthesis 140, which includes PS femoral component 10 (previously described for FIG. 6 and shown in FIGS. 6 and 14), a mobile PS insert 40 (FIG. 15) and mobile tibial component 80 (previously described for FIG. 12 and shown in FIGS. 12 and 16). Mobile PS insert 40 includes a superior surface 46 and a spine 42 that may be identical to superior surface 36 and spine 32 of fixed PS insert 30 shown in FIG. 7. Mobile PS insert 40 also includes an inferior surface 44 that may be identical to inferior surface 64 of mobile CR insert 60 shown in FIG. 11. An inferior surface 44 of mobile PS insert 40 articulates against platform 82 of mobile tibial component 80. A post 48 extends inferiorly from inferior surface 44 and rotatably inserts into hollow stem of mobile tibial component 80.

FIG. 17 is a chart representing an integrated, knee prosthesis system 40 that includes each of the knee prostheses shown in FIGS. 1, 5, 9 and 13. Each of components 10, 20, 30, 40, 50, 60, 70 and 80 may be provided in a plurality of sizes (for example, ten sizes) to accommodate the wide variation of anatomies of the patient population. These components may be matched together as follows:

Any one size of PS femoral component 10 may be matched with any one size of either fixed PS insert 30 or mobile insert 40.

Any one size of CR femoral component 20 may be matched with any one size of either fixed CR insert 50 or mobile CR insert 60.

Any one size of fixed tibial component 70 may be matched with any one size of either fixed PS insert 30 or fixed CR insert 50.

Any one size of mobile tibial component 80 may be matched with any one size of either mobile PS insert 40 or mobile CR insert 60.

In addition, each size of each of inserts 30, 40, 50 and 60 may be provided in a plurality of thicknesses.

As noted earlier, the anatomies of patients vary not only in size, but also in femur/tibia, size proportionality. Using historical data for TKR procedures, it is possible to determine the size combinations that would be needed for the majority of patients in the worldwide population. For example, each of practically all patients may be accommodated with a knee prosthesis distinctly-sized to fit both the femur and the tibia by pairing a femoral component that is sized either up two sizes or down two sizes from a tibial component. A "size 3" CR femoral component may be used with any one of a "size 1, 2, 3, 4 or 5" tibial components (fixed or mobile), whereas a "size 1" CR femoral component may be used with any one of a "size 1, 2 or 3" tibial components (fixed or mobile). Similarly, a "size 5" fixed tibial component may be used with any one of a "size 3, 4, 5, 6 or 7" fixed insert (CR or PS). Using knee prosthesis system 100, each of these pairings allows optimally matching the femoral component to the insert to maintain desirable geometrical relationships.

Tables 1 lists the components of an exemplary embodiment of knee prosthesis system 100. Table 2 lists the femoral component sizes provided for each femoral component listed in Table 1. Table 2 also shows for each femoral component size the compatible insert size for each insert listed in Table 1 and the compatible tibial component sizes for each tibial component listed in Table 1.

TABLE 1

Knee Prosthesis System Components

| Component | No. of sizes | No. of Thicknesses | No. of components |
|---|---|---|---|
| PS femoral (right) | 14 | — | 14 |
| PS femoral (left) | 14 | — | 14 |
| CR femoral (right) | 14 | — | 14 |
| CR femoral (left) | 14 | — | 14 |
| PS insert, mobile | 10 | 9 | 90 |
| PS insert, fixed | 10 | 9 | 90 |
| CR insert, mobile | 10 | 8 | 80 |
| CR insert, fixed | 10 | 8 | 80 |
| Tibial, mobile | 10 | — | 10 |
| Tibial, fixed | 10 | — | 10 |
| TOTAL | | | 416 |

TABLE 2

Compatible Sizes

| Femoral Component Size | Insert Size | Tibial Component Size |
|---|---|---|
| 1 | 1 | 1, 2, 3 |
| 2 | 2 | 1, 2, 3, 4 |
| 3 | 3 | 1, 2, 3, 4, 5 |
| 3N | 3 | 1, 2, 3, 4, 5 |
| 4 | 4 | 2, 3, 4, 5, 6 |
| 4N | 4 | 2, 3, 4, 5, 6 |
| 5 | 5 | 3, 4, 5, 6, 7 |
| 5N | 5 | 3, 4, 5, 6, 7 |
| 6 | 6 | 4, 5, 6, 7, 8 |
| 6N | 6 | 4, 5, 6, 7, 8 |
| 7 | 7 | 5, 6, 7, 8, 9 |
| 8 | 8 | 6, 7, 8, 9, 10 |
| 9 | 9 | 7, 8, 9, 10 |
| 10 | 10 | 8, 9, 10 |

The embodiment of knee prosthesis system 100 shown in Table 1 and Table 2 provides 2176 unique combinations of prosthesis components. In each of these combinations, the femoral component is distinctly-sized to fit the patient's femur while optimally matched to the insert, and the tibial component is distinctly-sized to fit the patient's tibia while compatible with the insert. As a result, knee prosthesis system 100 may allow surgeons to avoid compromising kinematic performance and life of the implanted joint for each patient of the worldwide patient population.

As previously noted, patella components may also be provided for implantation in combination with the knee prosthesis. The patella components may be provided in a plurality of sizes. Examples of patella implants that may be adapted for use in knee prosthesis system 100 are the "P.F.C. Sigma Patellar Implants" available from DePuy Orthopaedics, Inc., Warsaw, Ind. Another embodiment of knee prosthesis system 100 may also include two unique types of patella components, each type having five sizes, thereby allowing the surgeon to select from 21,760 unique combinations of components. In each of these combinations, the femoral component is distinctly-sized to match the patient's femur while optimally matched to the insert, and the tibial component is distinctly-sized to fit the patient's tibia while compatible with the insert.

Knee prosthesis system 100 allows the surgeon to select a combination of knee prosthesis components for implantation into the patient, wherein the components are distinctly-sized to fit the femur and tibia of the patient, while also optimally matched to avoid compromising performance of the reconstructed joint. Knee prosthesis system 100 further provides PS femoral components that are proportionally sized to the femur since the PS insert (fixed or mobile) is matched to each PS femoral component. Knee prosthesis system 100 also may lower the cost and complexity of the necessary inventory of implant components to accommodate the worldwide patient population, due primarily to the interchangeability of the components.

As previously explained, there is a need for a knee prosthesis system that has mobile and fixed tibial components with stems of different lengths, but that does not require several different reaming instruments for preparing the tibia. As shown in FIG. 17, mobile tibial component 80 and fixed tibial component 70 may have an approximately similar or identical external size and configuration for each anatomical size, enabling the surgeon to prepare the proximal tibia in approximately the same way using the same instrumentation.

This also allows the surgeon to implant either type of tibial component even after the proximal tibial has been surgically prepared.

Figure 18:
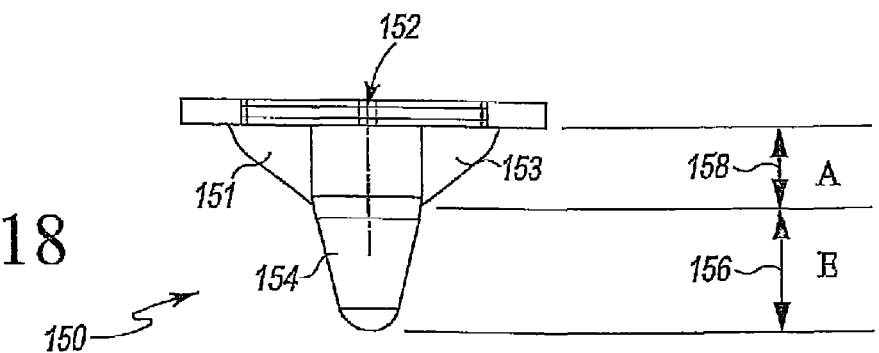
FIG. 18 is an anterior view of a size one, mobile tibial component.

FIGS. 18, 19, 20 and 21 show four representative sizes of mobile tibial component 80 of knee prosthesis system 100. Knee prosthesis system 100, for example, may have ten sizes of each of fixed tibial component 70 and mobile tibial component 80, as shown in Table 2. FIG. 18 is an anterior view of a size one, mobile tibial component 150 having a size one platform 152, a size one stem 154 and a pair of opposing keels 151, 153 extending between stem 154 and platform 152. Stem 154 has a distal portion 156 with a length "E" and a proximal portion 158 with a length "A".

Figure 19:
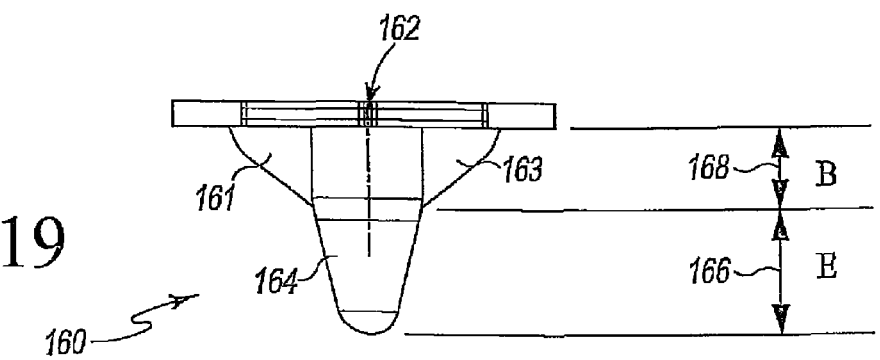
FIG. 19 is an anterior view of a size three, mobile tibial component.

FIG. 19 is an anterior view of a size three, mobile tibial component 160 having a size three platform 162, a size three stem 164 and a pair of opposing keels 161, 163. Stem 164 has a distal portion 166, also with length "E", and a proximal portion 168 with a length "B".

Figure 20:
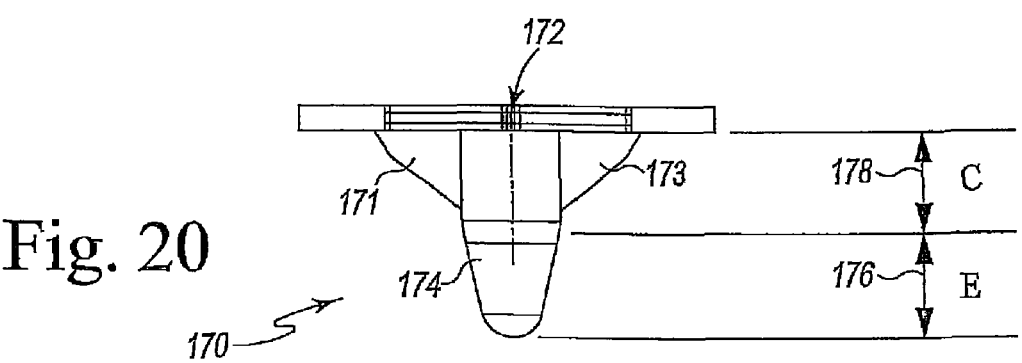
FIG. 20 is an anterior view of a size seven, mobile tibial component.

FIG. 20 is an anterior view of a size seven, mobile tibial component 170 having a size seven platform 172, a size three stem 174 and a pair of opposing keels 171, 173. Stem 174 has a distal portion 176, also with length "E", and a proximal portion 178 with a length "C".

Figure 21:
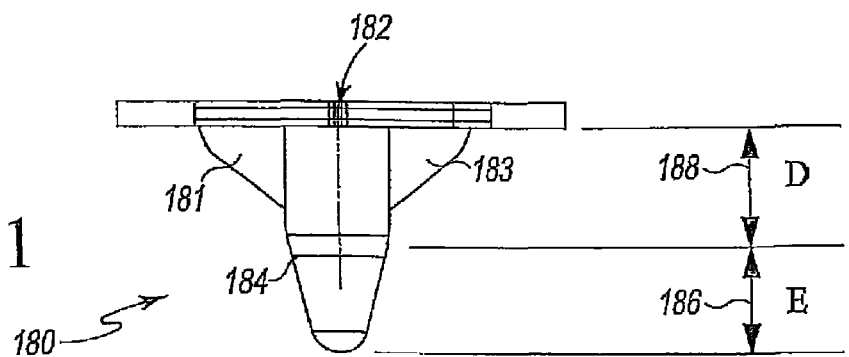
FIG. 21 is an anterior view of a size nine, mobile tibial component.

FIG. 21 is an anterior view of a size nine, mobile tibial component 180 having a size nine platform 182, a size nine stem 184 and a pair of opposing keels 181, 182. Stem 184 has a distal portion 186, also with length "E", and a proximal portion 188 with a length "D".

As shown in FIGS. 18, 19, 20 and 21, length "D" is greater than length "C", which is greater than length "B", which is greater than length "A". In general, increasing stem length corresponds to increasing length of the proximal portion of the stem, while the length of the distal portion remains constant.

Distal portions 156, 166, 176 and 186 of the stems 154, 164, 174, 184 may also have the same general shape. Proximal portions 158, 168, 178 and 188 may have approximately the same shape and vary primarily in length. The distal portions 156, 166, 176, 186 may have a generally conical or frustoconical shape. Keels 151, 153, 161, 163, 171, 173, 181, 183 may have approximately similar configurations and orientations. As would be apparent to those skilled in the art, a surgeon may use the same reaming instrument to form a cavity to the desired depth in the proximal tibia to receive any one of the various sizes of stems 154, 164, 174 and 184. Because the external sizes and configurations of each of the plurality of distinctly-sized fixed tibial components may be approximately similar or identical to the corresponding one of the plurality of distinctly-sized mobile tibial components, the surgical preparation of the proximal tibia may be the same for a given size of either the fixed or mobile tibial components, and the required instrumentation may be the same for all sizes of both the fixed and mobile tibial components.

As previously explained, it is also desirable that the total knee replacement system have mobile and fixed tibial components with a common, platform profile or "footprint" that is optimized for coverage of the tibial plateau, interaction with surrounding tissues, kinematic performance and other factors. FIGS. 22A, 22B, 23A, 23B, 24A, 24B, 25A and 25B show superior (plan) views of four representative sizes of fixed and mobile tibial components of knee prosthesis system 100. As noted previously, knee prosthesis system 100 may have ten sizes of each of fixed tibial component 70 and mobile tibial component 80, as shown in Table 2.

FIG. 22A shows size one mobile tibial component 150 to have a platform 152 that has a similar "footprint" or profile as a platform 252 of a size one fixed tibial component 250 shown in FIG. 22B.

FIG. 23A shows size three mobile tibial component 160 to have a platform 162 that has a similar profile as a platform 262 of a size one fixed tibial component 260 shown in FIG. 23B.

Figure 24B:
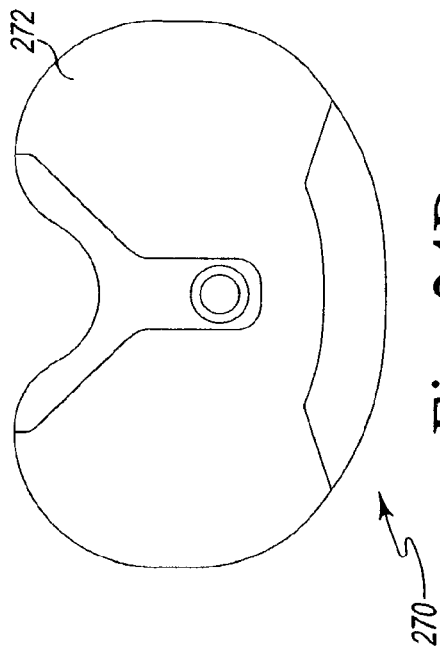
FIG. 24B is a superior view of a size seven, fixed tibial component.
Figure 24A:
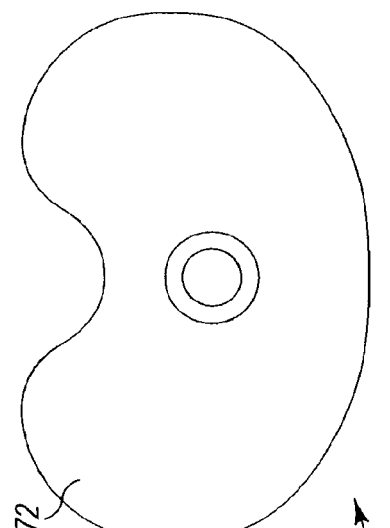
FIG. 24A is a superior view of the size seven, mobile tibial component of FIG. 20.

FIG. 24A shows size seven mobile tibial component 170 to have a platform 172 that has a similar profile as a platform 272 of a size one fixed tibial component 270 shown in FIG. 24B.

Figure 25B:
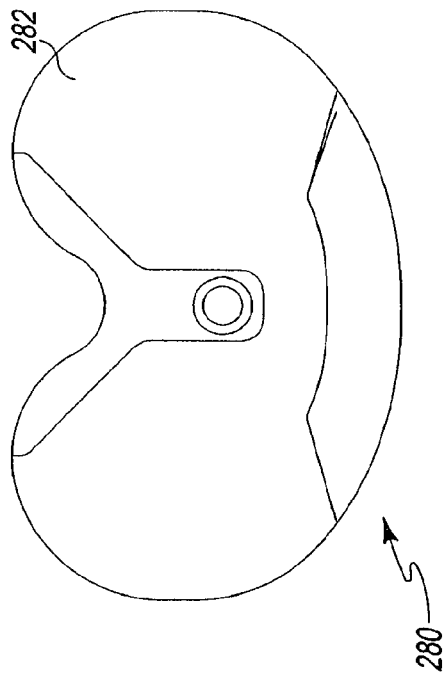
FIG. 25B is a superior view of a size nine, fixed tibial component.
Figure 25A:
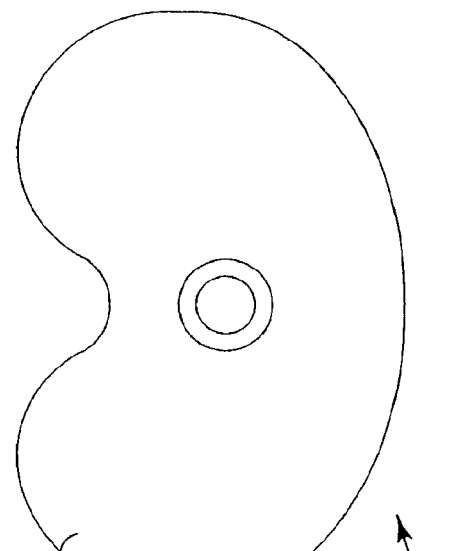
FIG. 25A is a superior view of the size nine, mobile tibial component of FIG. 21.

FIG. 25A shows size nine mobile tibial component 180 to have a platform 182 that has a similar profile as a platform 282 of a size one fixed tibial component 280 shown in FIG. 25B.

For each size of tibial component, the platform profile (as viewed from the top, in the direction of the stem axis) is the same for both mobile and fixed tibial components for a particular anatomical size. There is no need to change tibial component size to get the same, tibial plateau coverage when choosing between a mobile and a fixed prosthesis. Another benefit of the common platform shape is that the same casting tool or a portion of the tool may be used in the manufacture of both tibial components, enabling reduced component cost.

We have shown and described various embodiments and examples. However, a person having ordinary skill in the art may modify the methods and devices described herein without departing from the overall concept. For instance, the specific materials, dimensions and the scale of drawings should be understood to be non-limiting examples. Accordingly, we do not intend the scope of the following claims to be understood as limited to the details of structure, materials or acts shown and described in the specification and drawings.

We claim:

1. A knee prosthesis system for cruciate-retaining (CR) and posterior-stabilized (PS), total knee replacement procedures comprising:
   a. a plurality of differently-sized CR femoral components, each CR femoral component having a medial condyle surface and a lateral condyle;
   b. a plurality of differently-sized PS femoral components, each PS femoral component having a medial condyle surface and a lateral condyle surface;
   c. a plurality of differently-sized metal fixed tibial components;
   d. a plurality of differently-sized mobile tibial components;
   e. a plurality of differently-sized CR mobile inserts, each CR mobile insert having a medial bearing surface configured to articulate with the medial condyle surface of one size of CR femoral components and a lateral bearing surface configured to articulate with the lateral condyle surface of the same size of CR femoral components, wherein each size of CR mobile inserts may be mounted on at least two different sizes of the mobile tibial components;
   f. a plurality of differently-sized polymeric CR fixed inserts, each CR fixed insert having a medial bearing surface configured to articulate with the medial condyle surface of one size of CR femoral components and a lateral bearing surface configured to articulate with the lateral condyle surface of the same size of CR femoral components, wherein each size of CR fixed inserts has a different width and may be mounted in a secure fixed relationship with at least two different sizes of the fixed tibial components;
   g. a plurality of differently-sized polymeric PS fixed inserts, each PS fixed insert having a medial bearing surface configured to articulate with the medial condyle surface of one size of PS femoral components and a lateral bearing surface configured to articulate with the lateral condyle surface of the same size of PS femoral components, wherein each size of PS fixed inserts has a different width and may be mounted in a secure fixed relationship with at least two different sizes of the fixed tibial components; and h. a plurality of PS mobile inserts, each PS mobile insert having a medial bearing surface configured to articulate with the medial condyle surface of one size of PS femoral components and a lateral bearing surface configured to articulate with the lateral condyle surface of the same size of PS femoral components, wherein each size of PS mobile inserts may be mounted on at least two different sizes of the mobile tibial components;

i. wherein each tibial component has a platform and a stem extending distally from the platform, each stem having a distal portion and a proximal portion, the distal portion and the proximal portion having different shapes, the distal portion of the stem of each size of tibial component having the same length and the same generally conical shape and the proximal portion of the stem of each size of tibial component having a different length.

2. The knee prosthesis system of claim 1, wherein: each of the plurality of differently-sized fixed tibial components has a platform from which extends an anterior buttress and a posterior buttress for retaining any one of the plurality of PS fixed inserts and any one of the plurality of CR fixed inserts; the anterior buttresses and posterior buttresses of at least two sizes of fixed tibial components are commonly-sized and commonly-located; and each PS fixed insert has a lower surface with recesses defined therein to receive the anterior buttress and posterior buttress of at least two sizes of fixed tibial components and each CR fixed insert has a lower surface with recesses defined therein to receive the anterior buttress and posterior buttress of at least two sizes of fixed tibial components.

3. The knee prosthesis system of claim 1, wherein each of the plurality of PS fixed inserts and each of the plurality of PS mobile inserts have a surface and a spine extending superiorly therefrom, the spine having a posterior side including a concave cam surface and a convex cam surface, and the posterior cam of each PS femoral component includes a concave cam surface and a convex cam surface, wherein the concave cam surface of the posterior cam contacts the convex cam surface of the spine during a first range of flexion and the convex cam surface of the posterior cam contacts the concave cam surface of the spine during a second range of flexion.

4. The knee prosthesis system of claim 3, wherein each of the plurality of differently-sized PS femoral components includes an intracondylar notch and wherein the intracondylar notch of each of the differently-sized PS femoral components is proportionately sized and shaped to fit a particular anatomical size and shape of a patient's femur.

5. The knee prosthesis system of claim 1, further including a plurality of patella components, any one of which may be used in combination with any one of the plurality of differently-sized CR femoral components and in combination with any one of the plurality of differently-sized PS femoral components.

6. The knee prosthesis system of claim 1, wherein each of the plurality of CR fixed inserts, each of the plurality of CR mobile inserts, each of the plurality of PS fixed inserts and each of the plurality of PS mobile inserts, have a thickness different from the others within that plurality.

7. The knee prosthesis system of claim 1, wherein the stems for a particular anatomical size of the fixed and mobile tibial components have approximately the same external size and configuration, such that approximately the same surgical preparation of the proximal tibia is required for each of the fixed and the mobile tibial components for the particular anatomical size.

8. A knee prosthesis system for cruciate-retaining (CR) and posterior-stabilized (PS), total knee replacement procedures comprising:

a. a plurality of differently-sized CR femoral components;
b. a plurality of differently-sized PS femoral components;
c. a plurality of differently-sized fixed tibial components;
d. a plurality of differently-sized mobile tibial components;
e. a plurality of CR mobile inserts, each of which is sized and shaped such that each may be optimally matched to one of the CR femoral components;
f. a plurality of differently-sized polymeric CR fixed inserts, each of which has an articulation surface that is sized and shaped such that each may be optimally matched to one of the CR femoral components and each of which has an opposite surface with a different width;
g. a plurality of differently-sized polymeric PS fixed inserts, each of which has an articulation surface that is sized and shaped such that each may be optimally matched to one of the PS femoral components and each of which has an opposite surface with a different width;
h. a plurality of PS mobile inserts, each of which is sized and shaped such that each may be optimally matched to one of the PS femoral components;

wherein:
the fixed tibial components have mounting structures for securing a selected PS fixed insert or CR fixed insert and a selected one of the fixed tibial components together;
the mounting structures of at least two sizes of fixed tibial components are commonly-sized and commonly-located so that at least one size of CR fixed insert and at least one size of PS fixed insert may be selectively secured to at least two sizes of fixed tibial components; and
each tibial component has a platform and a stem extending distally from the platform, each stem having a distal portion and a proximal portion, the distal portion and the proximal portion having different shapes, the distal portion of the stem of each size of tibial component having the same length and the same generally conical shape and the proximal portion of the stem of each size of tibial component having a different length.

9. The knee prosthesis system of claim 8, further including a plurality of patella components, any one of which may be used in combination with any one of the plurality of differently-sized CR femoral components and in combination with any one of the plurality of differently-sized PS femoral components.

10. The knee prosthesis system of claim 8, wherein each of the differently-sized PS femoral components includes an intracondylar notch that is proportionately sized and shaped to fit a particular anatomical size and shape of a patient's femur.

11. The knee prosthesis system of claim 8, wherein the stems for a particular anatomical size of fixed and mobile tibial components have approximately the same external size and configuration, such that approximately the same surgical preparation of the proximal tibia is required for each of the fixed and the mobile tibial components for the particular anatomical size.

12. A knee prosthesis system for cruciate-retaining (CR) and posterior-stabilized (PS), total knee replacement procedures comprising:
   a. a plurality of fixed CR knee prostheses;
   b. a plurality of mobile CR knee prostheses;
   c. a plurality of fixed PS knee prostheses; and
   d. a plurality of mobile PS knee prostheses;
   wherein each fixed prosthesis represents a size combination and includes one of a plurality of differently-sized femoral components, one of a plurality of differently-sized tibial components, and one of a plurality of differently-sized inserts, and each prosthesis is optimally matched for performance with the size of the insert matching the size of the femoral component and the size of the tibial component being independent of the size of the femoral component, whereby the knee prosthesis system may be used for a variety of anatomies within a patient population; and wherein:
   the tibial components of the fixed CR knee prostheses and the fixed PS knee prostheses include platforms with buttresses;
   the buttresses of at least two sizes of tibial components of the fixed CR knee prostheses and the fixed PS knee prostheses are commonly sized and commonly located;
   each size of tibial component has a different width;
   the inserts of the fixed CR knee prostheses and the fixed PS knee prostheses comprise a polymeric material and include lower surfaces with recesses defined therein to receive the buttresses of the tibial components of the fixed CR knee prostheses and the fixed PS knee prostheses;
   each size of insert of the fixed CR knee prostheses and fixed PS knee prostheses has a different width;
   each insert of the fixed CR knee prostheses and the fixed PS knee prostheses may be mounted in a secure fixed relationship with at least two different sizes of the tibial components of the fixed CR knee prostheses and the fixed PS knee prostheses; and
   each tibial component has a platform and a stem extending distally from the platform, each stem having a distal portion and a proximal portion, the distal portion and the proximal portion having different shapes, the distal portion of the stem of each size of tibial component having the same length and the same generally conical shape and the proximal portion of the stem of each size of tibial component having a different length.

13. A knee prosthesis system for cruciate-retaining (CR) and posterior-stabilized (PS), total knee replacement procedures comprising:
   a. a plurality of differently-sized CR femoral components;
   b. a plurality of differently-sized PS femoral components;
   c. a plurality of differently-sized fixed tibial components and a plurality of differently-sized mobile tibial components;
   d. a plurality of differently-sized polymeric CR fixed inserts;
   e. a plurality of differently-sized polymeric PS fixed inserts;
   f. a plurality of differently-sized CR mobile inserts; and
   g. a plurality of differently-sized PS mobile inserts;
   wherein:
      each size CR femoral component is compatible with a single size of CR fixed insert;
      each size CR femoral component is compatible with a single size of CR mobile insert;
      each size of PS femoral component is compatible with a single size of PS fixed insert;
      each size of PS femoral component is compatible with a single size of PS mobile insert;
      each size of fixed tibial component has a different width;
      each size of CR fixed insert has a different width;
      each size of PS fixed insert has a different width;
      the tibial components and inserts have complementary mounting structures so that each size of CR fixed insert can be mounted in a secure fixed relationship on a plurality of sizes of fixed tibial components, each size of CR mobile insert is compatible with a plurality of sizes of mobile tibial components, each size of PS fixed insert can be mounted in a secure fixed relationship on a plurality of sizes of fixed tibial components and each size of PS mobile insert is compatible with a plurality of sizes of mobile tibial components; and
      each tibial component has a platform and a stem extending distally from the platform, each stem having a distal portion and a proximal portion, the distal portion and the proximal portion having different shapes, the distal portion of the stem of each size of tibial component having the same length and the same generally conical shape and the proximal portion of the stem of each size of tibial component having a different length.

14. The knee prosthesis system of claim 13, wherein the stems for a particular anatomical size of fixed and mobile tibial components have approximately the same external size and configuration, such that approximately the same surgical preparation of the proximal tibia is required for each of the fixed and the mobile tibial components for the particular anatomical size.

15. The knee prosthesis system of claim 13, wherein each of the plurality of differently-sized fixed tibial components has a platform from which extends an anterior buttress and a posterior buttress for retaining any one of the plurality of PS fixed inserts and any one of the plurality of CR fixed inserts.

16. The knee prosthesis system of claim 13, wherein each of the plurality of PS fixed inserts and each of the plurality of PS mobile inserts has a surface and a spine extending superiorly therefrom, the spine having a posterior side including a concave cam surface and a convex cam, and wherein each of the plurality of differently-sized PS femoral components includes a pair of spaced-apart condyles defining an intracondylar notch therebetween and a posterior cam positioned in the intracondylar notch, the posterior cam including a concave cam surface and a convex cam surface, wherein the concave cam surface of the posterior cam contacts the convex cam surface of the spine during a first range of flexion and the convex cam surface of the posterior cam contacts the concave cam surface of the spine during a second range of flexion.

17. The knee prosthesis system of claim 16, wherein the intracondylar notch of each of the differently-sized PS femoral components is proportionately sized and shaped to fit a particular anatomical size and shape of a patient's femur.

18. The knee prosthesis system of claim 13, wherein each of the plurality of CR fixed inserts, each of the plurality of CR mobile inserts, each of the plurality of PS fixed inserts and each of the plurality of PS mobile inserts, have a thickness different from the others within that plurality.

19. The knee prosthesis system of claim 13, further including a plurality of patella components, any one of which may be used in combination with any one of the plurality of differently-sized CR femoral components and in combination with any one of the plurality of differently-sized PS femoral components.

\* \* \* \* \*